United States Patent [19]
Tohyama et al.

[11] Patent Number: 6,107,250
[45] Date of Patent: Aug. 22, 2000

[54] PYRIDAZIN-3-ONE DERIVATIVES AND THEIR USE

[75] Inventors: Yoshitomo Tohyama, Ashiya; Masayuki Enomoto, Takarazuka; Hisayuki Hoshi, Toyonaka, all of Japan

[73] Assignee: Sumitomo Chemical Company Limited, Osaka-fu, Japan

[21] Appl. No.: 09/026,403

[22] Filed: Feb. 19, 1998

[30] Foreign Application Priority Data

Feb. 20, 1997 [JP] Japan ................................ 9-036706

[51] Int. Cl.⁷ ................... A01N 43/58; C07D 237/14; C07D 237/16
[52] U.S. Cl. ............................. 504/238; 544/239
[58] Field of Search ................ 504/238; 544/239

[56] References Cited

U.S. PATENT DOCUMENTS

| | | | |
|---|---|---|---|
| 4,411,691 | 10/1983 | Rohr et al. | 544/240 |
| 4,576,630 | 3/1986 | Parg et al. | 71/92 |
| 4,844,729 | 7/1989 | Becker et al. | 544/240 |
| 4,941,911 | 7/1990 | Freund et al. | 504/238 |

FOREIGN PATENT DOCUMENTS

| | | |
|---|---|---|
| WO 97/07104 | 2/1997 | European Pat. Off. |
| 2526643 | 12/1976 | Germany |
| 2808193 | 9/1979 | Germany |
| 3321007 | 12/1984 | Germany |
| 3617997 | 12/1987 | Germany |
| 19520613 | 12/1996 | Germany |

*Primary Examiner*—Emily Bernhardt
*Attorney, Agent, or Firm*—Sughrue, Mion, Zinn, Macpeak & Seas, PLLC

[57] ABSTRACT

The present invention provides novel pyridazin-3-one derivatives of general formula (1):

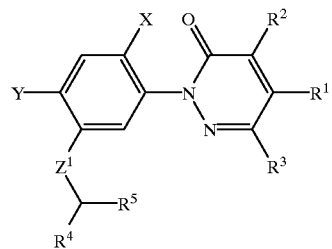

(1)

wherein $R^1$ is haloalkyl; $R^2$ and $R^3$ are independently hydrogen, alkl, haloalkyl, or alkoxyalkyl; X is hydrogen or halogen; Y is halogen, nitro, cyano, or trihalomethyl; $Z^1$ is oxygen, sulfur, $CH_2$, or NH; $R^4$ is hydrogen, halogen, or alkyl; and $R^5$ is cycoalkyl, formyl, benzyl, alkyl with an epoxy group, or other substituents as defined in the description, and herbicides containing them as active ingredients.

10 Claims, No Drawings

PYRIDAZIN-3-ONE DERIVATIVES AND THEIR USE

FIELD OF INVENTION

The present invention relates to pyridazin-3-one derivatives having excellent herbicidal activity and their use.

SUMMARY OF THE INVENTION

The present inventors have extensively studied to seek out some compounds having excellent herbicidal activity. As a result, they have found that pyridazin-3-one derivatives of general formula (1) as depicted below have excellent herbicidal activity, thereby completing the present invention.

Thus, the present invention provides pyridazin-3-one derivatives (hereinafter referred to as the present compounds) of formula (1):

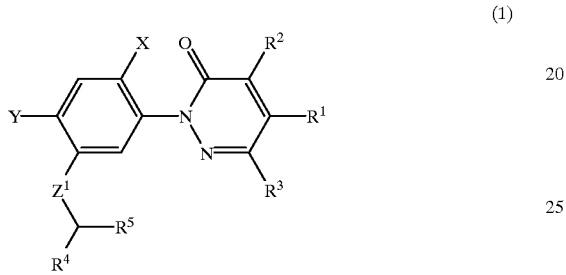

wherein $R^1$ is $C_1$–$C_3$ haloalkyl;

$R^2$ and $R^3$ are the same or different, and are independently hydrogen, $C_1$–$C_3$ alkyl, $C_1$–$C_3$ haloalkyl, or $C_1$–$C_3$ alkoxy $C_1$–$C_3$ alkyl;

X is hydrogen or halogen;

Y is halogen, nitro, cyano, or trihalomethyl;

$Z^1$ is oxygen, sulfur, $CH_2$, or NH;

$R^4$ is hydrogen, halogen or $C_1$–$C_6$ alkyl; and $R^5$ is $C_3$–$C_8$ cycloalkyl, formyl, benzyl, $C_2$–$C_{10}$ alkyl with an epoxy group, $C_3$–$C_8$ cycloalkyl $C_1$–$C_6$ alkyl, formyl $C_1$–$C_6$ alkyl, $C_3$–$C_8$ cycloalkyl $C_2$–$C_6$ alkenyl, formyl $C_2$–$C_6$ alkenyl, $C_1$–$C_6$ alkyl substituted with $OR^6$ and $OR^7$ on the same carbon atom, $C_2$–$C_6$ alkenyl substituted with $OR^6$ and $OR^7$ on the same carbon atom, $C_1$–$C_6$ alkyl substituted with $SR^6$ and $SR^7$ on the same carbon atom, $C_2$–$C_6$ alkenyl substituted with $SR^6$ and $SR^7$ on the same carbon atom, carboxy $C_2$–$C_6$ alkenyl, ($C_1$–$C_8$ alkoxy)carbonyl $C_2$–$C_6$ alkenyl, ($C_1$–$C_6$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl, ($C_3$–$C_8$ cycloalkoxy)carbonyl $C_2$–$C_6$ alkenyl, ($C_1$–$C_6$ alkyl)carbonyl $C_2$–$C_6$ alkenyl, ($C_1$–$C_6$ haloalkyl) carbonyl $C_2$–$C_6$ alkenyl, {($C_1$–$C_4$ alkoxy) $C_1$–$C_4$ alkyl}carbonyl $C_2$–$C_6$ alkenyl, or ($C_3$–$C_8$ cycloalkyl) carbonyl $C_2$–$C_6$ alkenyl;

$R^6$ and $R^7$ are the same or different, and are independently $C_1$–$C_6$ alkyl or $C_1$–$C_6$ haloalkyl, or $R^1$ and $R^7$ are taken together to form ethylene optionally substituted with halogen, trimethylene optionally substituted with halogen, tetramethylene optionally substituted with halogen, pentamethylene optionally substituted with halogen, or ethyleneoxyethylene optionally substituted with halogen; and herbicides containing them as active ingredients.

DETAILED DESCRIPTION OF THE INVENTION

Particular examples of the present compounds are as follows:

pyridazin-3-one derivatives wherein $Z^1$ is oxygen, sulfur, or NH, and $R^5$ is formyl, formyl $C_1$–$C_6$ alkyl, formyl $C_2$–$C_6$ alkenyl, $C_1$–$C_6$ alkyl substituted with $OR^6$ and $OR^7$ on the same carbon atom, $C_2$–$C_6$ alkenyl substituted with $OR^6$ and $OR^7$ on the same carbon atom, $C_1$–$C_6$ alkyl substituted with $SR^6$ and $SR^7$ on the same carbon atom, $C_2$–$C_6$ alkenyl substituted with $SR^6$ and $SR^7$ on the same carbon atom, ($C_1$–$C_6$ alkyl) carbonyl $C_2$–$C_6$ alkenyl, ($C_1$–$C_6$ haloalkyl) carbonyl $C_2$–$C_6$ alkenyl, {($C_1$–$C_4$ alkoxy) $C_1$–$C_4$ alkyl} carbonyl $C_2$–$C_6$ alkenyl, or ($C_3$–$C_8$ cycloalkyl) carbonyl $C_2$–$C_6$ alkenyl, $R^6$ and $R^7$ are the same or different, and are independently $C_1$–$C_6$ alkyl or $C_1$–$C_6$ haloalkyl;

pyridazin-3-one derivatives wherein $R^1$ is trifluoromethyl, $R^2$ is methyl or hydrogen, $R^3$ is hydrogen, X is fluorine, Y is chlorine, $R^4$ is hydrogen, and $R^5$ is $C_3$–$C_8$ cycloalkyl, benzyl, $C_2$–$C_{10}$ alkyl with an epoxy group, $C_3$–$C_8$ cycloalkyl $C_1$–$C_6$ alkyl, $C_3$–$C_8$ cycloalkyl $C_2$–$C_6$ alkenyl, $C_1$–$C_6$ alkyl substituted with $OR^6$ and $OR^7$ on the same carbon atom, $C_2$–$C_6$ alkenyl substituted with $OR^6$ and $OR^7$ on the same carbon atom, $C_1$–$C_6$ alkyl substituted with $SR^6$ and $SR^7$ on the same carbon atom, $C_2$–$C_6$ alkenyl substituted with $SR^6$ and $SR^7$ on the same carbon atom, carboxy $C_2$–$C_6$ alkenyl, ($C_1$–$C_8$ alkoxy)carbonyl $C_2$–$C_6$ alkenyl, ($C_1$–$C_6$ haloalkoxy)carbonyl $C_2$–$C_6$ alkenyl, {($C_1$–$C_4$ alkoxy) $C_1$–$C_4$ alkoxy}carbonyl $C_2$–$C_6$ alkenyl, or ($C_3$–$C_8$ cycloalkoxy)carbonyl $C_2$–$C_6$ alkenyl, $R^6$ and $R^7$ are taken together to form ethylene, trimethylene, tetramethylene, pentamethylene, or ethyleneoxyethylene;

pyridazin-3-one derivatives wherein $R^1$ is trifluoromethyl, $R^2$ is methyl or hydrogen, $R^3$ is hydrogen, X is fluorine, Y is chlorine, $R^4$ is hydrogen, $R^5$ is $C_3$–$C_8$ cycloalkyl, $C_2$–$C_{10}$ alkyl with an epoxy group, ($C_1$–$C_8$ alkoxy) carbonyl $C_2$–$C_6$ alkenyl, or $C_1$–$C_6$ alkyl substituted with $OR^6$ and $OR^7$ on the same carbon atom, $R^6$ and $R^7$ are taken together to form ethylene or trimethylene;

pyridazine-3-one derivatives wherein $R^1$ is trifluoromethyl, $R^2$ is methyl or hydrogen, $R^3$ is hydrogen, X is fluorine, Y is chlorine, $R^4$ is hydrogen, and $R^5$ is $C_3$–$C_8$ cycloalkyl;

pyridazin-3-one derivatives wherein $Z^1$ is oxygen;

pyridazin-3-one derivatives wherein Y is halogen, $R^1$ is trifluoromethyl, $R^2$ is hydrogen or methyl, $R^3$ is hydrogen, and $R^4$ is hydrogen or methyl;

pyridazin-3-one derivatives wherein X is fluorine;

pyridazin-3-one derivatives wherein $Z^1$ is oxygen, sulfur, or NH;

pyridazin-3-one derivatives wherein $R^4$ is hydrogen; and pyridazin-3-one derivatives wherein $R^5$ is formyl or $C_1$–$C_6$ alkyl substituted with $OR^6$ and $OR^7$ on the same carbon atom, $R^6$ and $R^7$ are the same or different, and are independently $C_1$–$C_6$ alkyl or $C_1$–$C_6$ haloalkyl.

The halogen represented by X or Y may include chlorine, fluorine, and bromine.

The trihalomethyl represented by Y may include trifluoromethyl.

The $C_1$–$C_3$ haloalkyl represented by $R^1$ may include trifluoromethyl, chlorodifluoromethyl, and pentafluoroethyl.

The $C_1$–$C_3$ alllyl represented by $R^2$ or $R^3$ may include methyl, ethyl, and isopropyl.

The $C_1$–$C_3$ haloalkyl represented by $R^2$ or $R^3$ may include trichloromethyl, triuoromethyl, difluoromethyl, chlorodifluoromethyl and pentafluoroethyl.

The $C_1$–$C_3$ alkoxy $C_1$–$C_3$ alkyl represented by $R^2$ or $R^3$ may include methoxymethyl.

The $C_1$–$C_6$ alhyl represented by $R^4$ may include methyl, ethyl, propyl, butyl, and amyl;

The halogen represented by $R^4$ may include chlorine, fluorine, and bromine.

The $C_3$–$C_8$ cycloalkyl represented by $R^5$ may include cyclopropyl, cyclobutyl, cyclopentyl, and cyclohexyl.

The $C_2$–$C_{10}$ alkyl with an epoxy group represented by $R^5$ may include 1,2-epoxyethyl, 1,2-epoxypropyl, 2,3-epoxypropyl, and 3,4-epoxybutyl.

The $C_3$–$C_8$ cycloalkyl $C_1$–$C_6$ alkyl represented by $R^5$ may include cyclopropylmethyl, 2-(cyclopropyl)ethyl, cyclobutylmethyl, cyclopentylmethyl, and cyclohexylmethyl.

The formyl $C_1$–$C_6$ alkyl represented by $R^5$ may include formylmethyl, 2-formylethyl, and 3-formylpropyl.

The $C_3$–$C_8$ cycloalkyl $C_2$–$C_6$ alkenyl may include 2-cyclopropylvinyl, 3-cyclopropyl-1-propenyl, and 3-cyclobutyl-1-propenyl.

The formyl $C_2$–$C_6$ alkenyl represented by $R^5$ may include 2-formylvinyl and 2-formyl-1-propenyl.

The $C_1$–$C_6$ alkyl substituted with $OR^6$ and $OR^7$ on the same carbon atom represented by $R^5$ may include dimethoxymethyl, diethoxymethyl, dipropoxymethyl, ethylenedioxymethyl, trimethylenedioxymethyl, 2,2-dimethoxyethyl, 2,2-diethoxyethyl, 2,2-ethylenedioxymethyl, 2,2-trimethylenedioxymethyl, 3,3-dimethoxypropyl, 3,3-diethoxypropyl, 3,3-ethylenedioxypropyl, and 3,3-trimethylenedioxymethyl.

The $C_2$–$C_6$ alkenyl substituted with $OR^6$ and $OR^7$ on the same carbon atom represented by $R^5$ may include 3,3-dimethoxy-1-propenyl and 3,3-diethoxy-1-propenyl.

The $C_1$–$C_6$ alkyl substituted with $SR^6$ and $SR^7$ on the same carbon atom represented by $R^5$ may include di(methylthio)methyl, di(ethylthio)methyl, di(propylthio)methyl, ethylenedithiomethyl, trimethylenedithiomethyl, 2,2-di(methylthio)ethyl, 2,2-di(ethylthio)ethyl, 2,2-ethylenedithioethyl, 2,2-trimethylenedithioethyl, 3,3-di(methylthio)propyl, 3,3-di(ethylthio)propyl, 3,3-ethylenedithiopropyl, and 3,3-trimethylenedithiopropyl.

The $C_2$–$C_6$ alkenyl substituted with $SR^6$ and $SR^7$ on the same carbon atom represented by $R^5$ may include 3,3-dimethylthio-1-propenyl and 3,3-diethylthio-1-propenyl.

The carboxy $C_2$–$C_6$ alkenyl represented by $R^5$ may include 2-carboxyvinyl and 2-carboxy-1-propenyl.

The ($C_1$–$C_8$ alkoxy)carbonyl $C_2$–$C_6$ alkenyl represented by $R^5$ may include 2-methoxycarbonylvinyl, 2-ethoxycarbonylvinyl, 2-propoxycarbonylvinyl, 2-isopropoxycarbonylvinyl, 2-methoxycarbonyl-1-propenyl, 2-ethoxycarbonyl-1-propenyl, 2-propoxycarbonyl-1-propenyl, and 2-isopropoxycarbonyl-1-propenyl.

The ($C_1$–$C_6$ haloalkoxy)carbonyl $C_2$–$C_8$ alkenyl represented by $R^5$ may include 2-chloro-2-ethoxycarbonylvinyl.

The {($C_1$–$C_4$ alkoxy) $C_1$–$C_4$ alkoxy}carbonyl $C_2$–$C_6$ alkenyl represented by $R^5$ may include 2-methoxymethoxycarbonylvinyl and 2-methoxymethoxycarbonyl-1-propenyl.

The ($C_3$–$C_8$ cycloalkoxy)carbonyl $C_2$–$C_6$ alkenyl represented by $R^5$ may include 2-cyclopropyloxycarbonylvinyl, 2-cyclobutyloxycarbonylvinyl, 2-cyclopentyloxycarbonylvinyl, 2-cyclopropyloxycarbonyl-1-propenyl, 2-cyclobutyloxycarbonyl-1-propenyl, and 2-cyclopentyloxycarbonyl-1-propenyl.

The ($C_1$–$C_6$ alkyl)carbonyl $C_2$–$C_6$ alkenyl represented by $R^5$ may include 2-methylcarbonylvinyl.

The ($C_1$–$C_6$ haloalkyl)carbonyl $C_2$–$C_6$ alkenyl represented by $R^5$ may include 2-chloromethylcarbonylvinyl.

The {($C_1$–$C_4$ alkoxy) $C_1$–$C_4$ alkyl}carbonyl $C_2$–$C_6$ alkenyl represented by $R^5$ may include 2-(2-methoxyethyl)carbonylvinyl.

The ($C_3$–$C_8$ cycloalkyl)carbonyl $C_2$–$C_6$ alkenyl represented by $R^5$ may include 2-cyclopropylcarbonylvinyl.

In the present compounds, preferred examples of the substituents in view of herbicidal activity are as follows:

fluorine, chlorine, and hydrogen for X, particularly fluorine;

chlorine for Y;

a group of $CF_2J$ wherein J is hydrogen, fluorine, chlorine, or trifluoromethyl, for $R^1$, more preferably trifluoromethyl;

methyl and hydrogen for $R^2$;

methyl and hydrogen for $R^3$; and methyl and hydrogen for $R^4$.

Particularly preferred examples of the present compounds are those wherein $R^1$ is trifluoromethyl, $R^2$ is methyl or hydrogen, $R^3$ is hydrogen, X is fluorine, Y is chlorine, $Z^1$ is oxygen, $R^4$ is hydrogen, and $R^5$ is of the formula:

For the present compounds, there may exist geometrical isomers based on the presence of a double bond or optical isomers based on the presence of at least one asymmetric carbon atom, and all of these geometrical and optical isomers are, of course, included within the scope of the present invention.

The present compounds can be produced, for example, by Production Processes 1 to 3 as described below.

(Production Process 1)

This is the production process according to the following scheme 1:

SCHEME 1 wherein X, Y, $R^1$, $R^2$, $R^3$, $R^4$, and $R^5$ are as defined above, and $Z^2$ is oxygen, sulfur, or NH.

The reaction conditions in the above step are, for example, as follows:

Compound [II] can be produced by reacting compound [I] with a compound of the formula:

CHZ(R⁴)R⁵ wherein Z is bromine, chlorine, iodine, methanesulfonyloxy, trifluoromethanesulfonyloxy, or p-toluenesulfonyloxy, $R^4$ and $R^5$ are as defined above, in the presence of a base, if necessary.

or recrystallization. Thus, the desired compound can be isolated.

(Production Process 2)

This is the production process according to the following scheme 2:

SCHEME 2

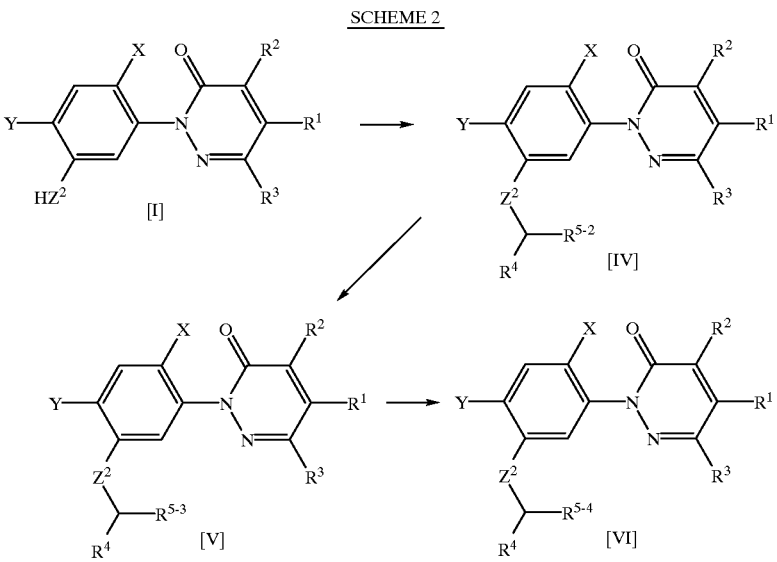

The reaction is effected without solvent or in a solvent. The reaction temperature is usually in the range of −20° to 150° C. The reaction time is usually in the range of a moment to 72 hours. The amounts of reagents to be used in the reaction are 1 mole of compound CHZ(R⁴)R⁵ and 1 mole of the base used, if necessary, relative to 1 mole of compound [I], which is the stoichiometric ratio but can be freely changed depending upon the reaction conditions.

The solvent which can be used may include aliphatic hydrocarbons such as hexane, cyclohexane, and petroleum ether; aromatic hydrocarbons such as benzene, toluene, and xylene; ethers such as diethyl ether, 1,4-dioxane, and tetrahydrofuran (hereinafter referred to as THF); acid amides such as formamide and N,N-dimethylformamide; tertiary amines such as pyridine, triethylamine, and N,N-dimethylaniline; sulfur compounds such as dimethylsulfoxide and sulforane; and mixtures thereof.

The base which can be used, if necessary, may include inorganic bases such as sodium hydrogencarbonate, potassium hydrogencarbonate, sodium carbonate, potassium carbonate, sodium hydroxide, potassium hydroxide, sodium hydride, and potassium hydride; organic bases such as triethylamine, diisopropylethylamine, pyridine, 4-dimethylaminopyridine, picoline, and N,N-dimethylaniline; and mixtures thereof.

The reaction may further involve the presence of an iodine compound, if necessary, such as potassium iodide or sodium iodide.

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography wherein X, Y, $R^1$, $R^2$, $R^4$, and $Z^2$ are as defined above, $R^{5-2}$ is $C_2$–$C_7$ alkenyl, $R^{5-3}$ is a substituent obtained by oxidative cleavage of the double bond of $R^{5-2}$ into a ketone or aldehyde moiety, such as formyl or formyl $C_1$–$C_6$ alkyl, $R^{5-4}$ is a substituent obtained by conversion of the ketone or aldehyde moiety into an acetal or thioacetal moiety with an alcohol or mercaptan, i.e., $C_1$–$C_6$ alkyl substituted with $OR^6$ and $OR^7$ on the same carbon atom, or $C_1$–$C_6$ alkyl substituted with $SR^6$ and $SR^7$ on the same carbon atom, wherein $R^6$ and $R^7$ are as defined above.

The reaction conditions in each step are, for example, as follows:

Step of Producing Compound [IV] from Compound [I]

Compound [IV] can be produced according to the process described in the Production Process 1.

Step of Producing Compound [V] from Compound [IV]

Compound [V] can be produced by treating compound [IV]with ozone prepared with an ozone generator) and then with a reducing agent.

The reaction is effected in a solvent. The reaction temperature is usually in the range of −78° to −40° C. The reaction time is usually in the range of a moment to 6 hours.

The solvent which can be used may include aliphatic hydrocarbons such as hexane, cyclohexane, and petroleum ether; halogenated hydrocarbons such as dichloromethane, chloroform, and 1,2-dichloroethane; aromatic hydrocarbons such as benzene, toluene, and xylene; ketones such as acetone, methyl ethyl ketone, methyl isobutyl ketone, and cyclohexanone; esters such as ethyl formate, ethyl acetate, and diethyl carbonate; alcohols such as methanol, ethanol, isopropanol, and butanol; and mixtures thereof.

The reducing agent which can be used may include metals such as zinc; disulfides such as dimethyl sulfide, diethyl sulfide, and dibutyl sulfide; phosphites such as trimethyl phosphite, triethyl phosphite, and tributyl phosphite; triarylphosphines such as triphenylphosphine; and trialkylphosphines such as tributylphosphine.

The reducing agent is usually used at an amount ranging from 1 mole to an excess relative to 1 mole of the starting material compound [IV].

Compound [V] can also be produced by reacting compound [IV] with osmium tetraoxide and sodium periodate.

The reaction is effected in a solvent. The reaction temperature is usually in the range of 0° to 60° C. The reaction time is usually in the range of a moment to 24 hours.

The solvent which can be used may include halogenated hydrocarbons such as dichloromethane, chloroform, and 1,2-dichloroethane; ethers such as 1,4-dioxane, THF, and diethyl ether; ketones such as acetone, methyl ethyl ketone, methyl isobutyl ketone, and cyclohexanone; esters such as ethyl formate, ethyl acetate, and diethyl carbonate; alcohols such as methanol, ethanol, isopropanol, and butanol; and mixtures thereof.

The osmium tetraoxide is usually used at an amount ranging from a catalytic amount to 1 mole relative to 1 mole of compound [IV]. The sodium periodate is usually used at an amount of 1 to 10 moles relative to 1 mole of compound [IV].

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

Step of Producing Compound [VI] from Compound [V]

Compound [VI] can be produced by reacting compound [V] with a corresponding alcohol (a compound of the general formula: $R^6OH$, $R^7OH$, or $HO—R^6—R^7—OH$, wherein $R^6$ and $R^7$ are as defined above, such as methanol, ethanol, ethylene glycol, or trimethylene glycol) or mercaptan (a compound of the formula: $R^6SH$, $R^7SH$, or $HS—R^6—R^7—SH$, wherein $R^6$ and $R^7$ are as defined above) in the presence of an acid catalyst to form an acetal or thioacetal.

The reaction is effected without solvent or in a solvent. The reaction time is usually in the range of a moment to 48 hours. The alcohol or mercaptan is usually used at an amount ranging from 1 mole to a large excess relative to 1 mole of compound [V].

The solvent which can be used may include aliphatic hydrocarbons such as hexane, cyclohexane, and petroleum ether; aromatic hydrocarbons such as benzene, toluene, and xylene; halogenated hydrocarbons such as dichloromethane, chloroform, and 1,2-dichloroethane; and mixtures thereof.

The acid catalyst which can be used may include sulfonic acids such as p-toluenesulfonic acid, benzenesulfonic acid, methanesulfonic acid, and trifluoromethanesulfonic acid; inorganic acids such as sulfuric acid, hydrogen chloride, and hydrogen bromide; Lewis acids such as zinc chloride and boron trifluoride-diethyl ether complex; and mixtures thereof.

The acid catalyst is usually used at an amount ranging from a catalytic amount to 5 moles relative to 1 mole of compound [V].

The formation of an acetal with an alcohol may also be effected in the presence of an orthoformate at an amount ranging from a catalytic amount to an excess.

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

(Production Process 3)

This is the production process according to the following scheme 3:

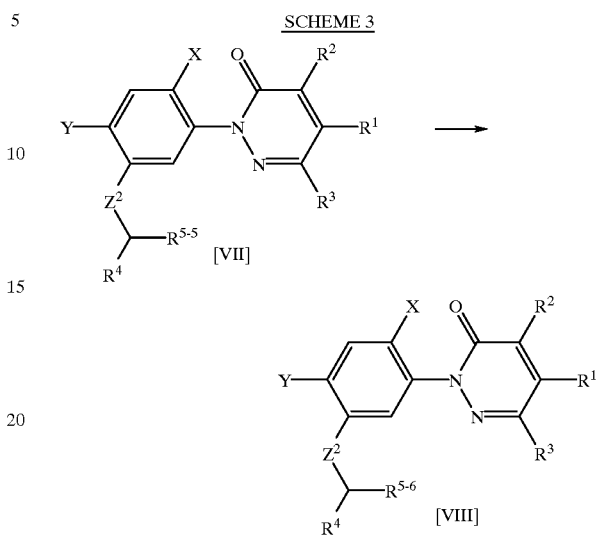

wherein X, Y, $R^1$, $R^2$, $R^3$, $R^4$, and $Z^2$ are as defined above, $R^{5-5}$ is $C_2$–$C_{10}$ alkenyl, and $R^{5-6}$ is $C_2$–$C_{10}$ alkyl with an epoxy group.

Compound [VII] can be produced according to the process described in the Production Process 1.

Compound [VIII] can be produced by treating compound [VII] with an oxidizing agent in the presence or absence of a base.

The reaction is effected in a solvent. The reaction temperature is usually in the range of –20° C. to 50° C. The reaction time is usually in the range of a moment to 48 hours.

The solvent which can be used may include halogenated hydrocarbons such as dichloromethane, chloroform, and 1,2-dichloroethane; alcohols such as methanol, ethanol, isopropanol, and butanol; benzene; water; and mixtures thereof.

The base which can be used may include sodium hydroxide, sodium hydrogencarbonate, potassium hydrogencarbonate, sodium carbonate, potassium carbonate, and tri-t-butoxy aluminum.

The oxidizing agent which can be used may include hydrogen peroxide, m-chloroperbenzoic acid, trifluoroperacetic acid, peracetic acid, t-butyl hydroperoxide, and sodium hyperchlorite.

The oxidizing agent is usually used at an amount of 1 to 50 moles relative to 1 mole of compound [VII]. The base is usually used at an amount of 0.1 to 5 moles relative to 1 mole of compound [VII].

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

The following will describe the production processes for the starting material compounds used in the production of the present compounds.

Compound [I] wherein $Z^2$ is oxygen or sulfur can be produced according to the following scheme 4.

SCHEME 4

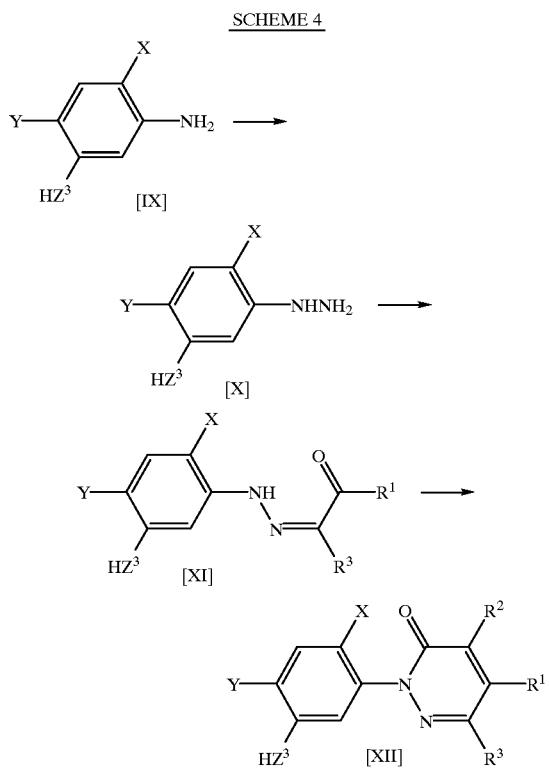

wherein X, Y, $R^1$, $R^2$, and $R^3$ are as defined above, and $Z^3$ is oxygen or sulfur.

The aniline derivative designated as compound [IX] in the above scheme is well known in the art, for example, in the published specification of European Patent Application, EP-61741-A, corresponding to U.S. Pat. No. 4,431,822 or can be produced according to the process disclosed therein.

Step of Producing Compound [X] from Compound [IX]

Compound [X] can be produced from compound [IX], for example, according to the following scheme 5 (see Organic Synthesis Collective, volume 1., p. 442).

SCHEME 5

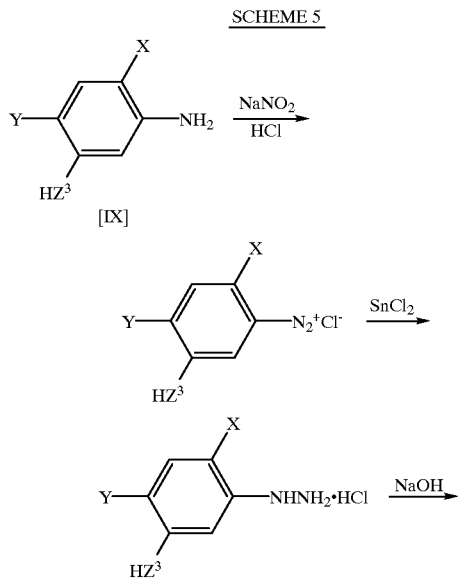

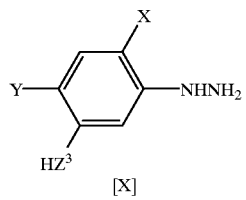

wherein X, Y, and $Z^3$ are as defined above.

Step of Producing Compound [XI] from Compound [X]

Compound [XI] can be produced by reacting an α-dihalo compound of the formula:

$$R^1C(=O)CV_2R^3$$

wherein $R^1$ and $R^3$ are as defined above, and V is iodine, bromine, or chlorine, with water in the presence of a base to give a carbonyl derivative of the formula:

$$R^1C(=O)C(=O)R^3$$

wherein $R^1$ and $R^3$ are as defined above (hereinafter referred to as reaction 1), and then reacting the carbonyl derivative with hydrazine derivative [X] (hereinafter referred to as reaction 2). The carbonyl derivative $R^1C(=O)C(=O)R^3$ can also be reacted as a hydrate in water or as an acetal derivative in an alcohol.

The reaction 1 is usually effected in a solvent (e.g., water). The reaction temperature is usually in the range of 0° to 100° C. The reaction time is usually in the range of a moment to 72 hours. The amounts of reagents to be used in the reaction are 2 moles of water and 2 moles of the base (e.g., sodium acetate) relative to 1 mole of α-dihalo compound $R^1C(=O)CV_2R^3$, which is the stoichiometric ratio but can be freely changed depending upon the reaction conditions.

The reaction 2 is usually effected in a solvent (e.g., THF). The reaction temperature is usually in the range of 0° to 100° C. The reaction time is usually in the range of a moment to 72 hours. The amounts of reagents to be used in the reaction are 1 mole of hydrazine derivative [X] relative to 1 mole of the α-dihalo compound used in the reaction 1, which is the stoichiometric ratio but can be freely changed depending upon the reaction conditions. The hydrazine derivative [X] may also be used in the form of a salt such as hydrochloride or sulfate.

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

Step of Producing Compound [XII] from Compound [XI]

Compound [XII] can be produced by reacting compound [XI] with a compound of the formula:

$$Ph_3P=C(R^2)COOC_2H_5$$

wherein $R^2$ is as defined above and Ph is phenyl.

The above compound $Ph_3P=C(R^2)COOC_2H_5$ is commercially available or can be produced according to the process described, for example, in the "Jikken Kagaku Koza" (published by Maruzen Kabushiki Kaisha), 4th edition, volume 24, pp. 259–260.

The reaction is usually effected in a solvent (e.g., THF). The reaction temperature is usually in the range of −20° to 150° C. The reaction time is usually in the range of a moment to 72 hours. The amounts of reagents to be used in the reactions are 1 mole of compound $Ph_3P=C(R^2)COOC_2H_5$ relative to 1 mole of compound [XI], which is the stoichiometric ratio but can be freely changed depending upon the reaction conditions.

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

Compound [I] wherein $Z^2$ is NH (i.e., compound [XVI]) can be produced according to the following scheme 6.

SCHEME 6

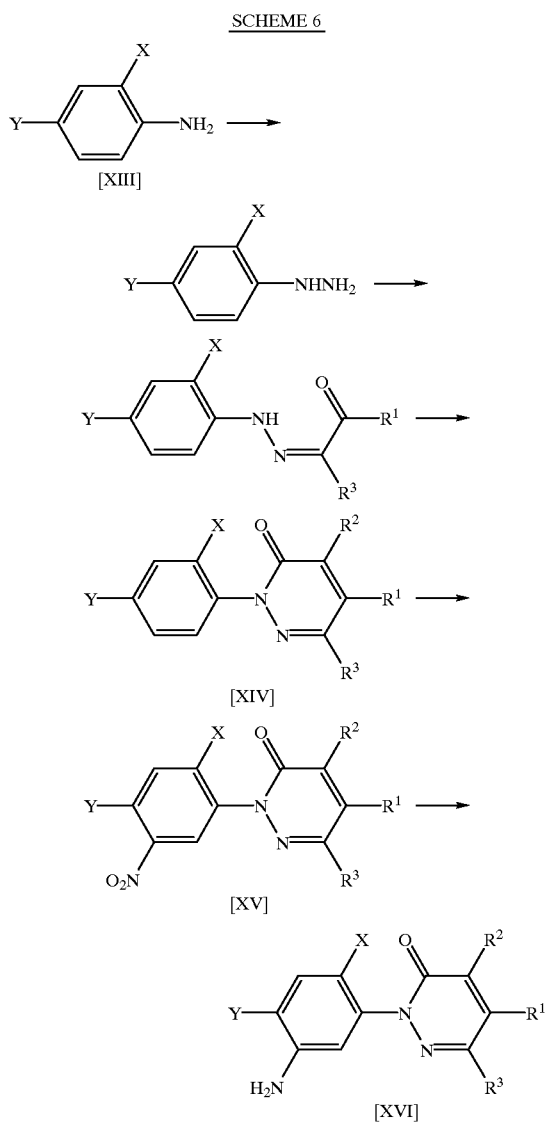

wherein X, Y, $R^1$, $R^2$, and $R^3$ are as defined above.

Step of Producing Compound [XIV] from Compound [XIII]

Compound [XIV] can be produced in the same manner as the process for producing compound [XII] from compound [XIII] (scheme 4).

Step of Producing Compound [XV] from Compound [XIV]

Compound [XV] can be produced by nitrating compound [XIV]. The reaction is usually effected in a solvent. The reaction temperature is usually in the range of –10° C. to room temperature. The reaction time is usually in the range of a moment to 72 hours.

The nitrating agent may include nitric acid and fuming nitric acid. The amounts of reagents to be used in the reaction are 1 mole of the nitrating agent relative to 1 mole of compound [XIV], which is the stoichiometric ratio but can be freely changed depending upon the reaction conditions.

The solvent which can be used in the reaction may include aliphatic hydrocarbons such as hexane, cyclohexane, and petroleum ether; ethers such as diethyl ether, 1,4-dioxane, and THF; acids such as sulfuric acid and acetic acid; and mixtures thereof.

After completion of the reaction, the reaction mixture is poured into ice water and the resulting crystals are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

Step of Producing Compound [XVI] from Compound [XV]

Compound [XVI] can be produced by reducing compound [XV] with a metal such as iron.

The reaction is usually effected in the presence of an acid in a solvent. The reaction temperature is usually in the range of room temperature to a heating temperature under reflux. The reaction time is usually in the range of a moment to 72 hours.

The reducing agent may include iron, zinc, and tin. The amounts of reagents to be used in the reaction are usually 3 moles to a large excess of the reducing agent relative to 1 mole of compound [XV].

The solvent which can be used in the reaction may include aliphatic hydrocarbons such as hexane, cyclohexane, and petroleum ether; aromatic hydrocarbons such as benzene, toluene, and xylene; ethers such as diethyl ether, 1,4-dioxane, and THF; esters such as ethyl formate, ethyl acetate, and diethyl carbonate; nitriles such as acetonitrile and benzonitrile; water; and mixtures thereof.

The acid which can be used may include acetic acid, hydrochloric acid, and sulfuric acid.

After completion of the reaction, the resulting crystals (deposited by the addition of water, if necessary) are collected by filtration, or the reaction mixture is subjected to ordinary post-treatments such as extraction with an organic solvent and concentration. If necessary, further purification may be carried out by a technique such as chromatography or recrystallization. Thus, the desired compound can be isolated.

The present compounds have excellent herbicidal activity and can exhibit excellent selectivity between crops and weeds.

For example, the present compounds have herbicidal activity against various weeds which may cause some trouble in the foliar treatment and soil treatment on upland fields, such as listed below.

Polygonaceous weeds:
wild buckwheat (*Polygonum convolvulus*), pale smartweed (*Polygonum lapathiolium*), pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceous weeds:

common purslane (*Portulaca oleracea*)

Caryophyllaceous weeds:

common chickweed (*Stellaria media*)

Chenopodiaceous weeds:

common lambsquarters (*Chenopodiunm album*), kochia (*Kochia scoparia*)

Amaranthaceous weeds:

redroot pigweed (*Amaranthus retroflexus*), smooth pigweed (*Amaranthus hybridus*)

Cruciferous (brassicaceous) weeds:

wild radish (*Raphanus raphanistrum*), wild mustard (*Sinapis arvensis*), shepherdpurse (*Capsella bursa-pastoris*)

Leguminous (fabaceous) weeds:

hemp sesbania (*Sesbania exaltata*), sicklepod (*Cassia obtusifolia*), Florida beggarweed (*Desmodium tortuosum*), white clover (*Trifolium repens*)

Malvaceous weeds:

velvetleaf (*Abutilon theophrasti*), prickly sida (*Sida spinosa*)

Violaceous weeds:

field pansy (*Viola arvensis*), wild pansy (*Viola tricolor*)

Rubiaceous weeds:

catchweed bedstraw (cleavers) (*Galium aparine*)

Convolvulaceous weeds:

ivyleaf morningglory (*Ipomoea hederacea*), tall morningglory (*Ipomoea purpurea*), entireleaf morningglory (*Ipomoea hederacea var. integriuscula*), pitted morningglory (*Ipomoea lacunosa*), field bindweed (*Convolvulus arvensis*)

Labiate weeds:

red deadnettle (*Lamium purpureum*), henbit (*Lamium amplexicaule*)

Solanaceous weeds:

jimsonweed (*Datura stramonium*), black nightshade (*Solanum nigrum*)

Scrophulariaceous weeds:

birdseye speedwell (*Veronica persica*), ivyleaf speedwell (*Veronica hederaefolia*)

Composite weeds:

common cocklebur (*Xanthium pensylvanicum*), common sunflower (*Helianthus annuus*), scentless chamomile (*Matricaria perforata or inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Ergeron canadensis*), Japanese mugwort (*Artemisia princeps*), tall goldenrod (*Solidago altissima*)

Boraginaceous weeds:

forget-me-not (*Myosotis arvensis*)

Asclepiadaceous weeds:

common milkweed (*Asclepias syriaca*)

Euphorbiaceous weeds:

sun spurge (*Euphorbia helioscopia*), spotted spurge (*Euphorbia maculata*)

Graminaceous weeds:

barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oats (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichoto-miflorum*), Texas panicum (*Panicum texanum*), shattercane (*Sorghum vulgare*)

Commelinaceous weeds:

common dayflower (*Commelina communis*)

Equisetaceous weeds:

field horsetail (*Equisetum arvense*)

Cyperaceous weeds:

rice flatsedge (*Cyperus iria*), purple nutsedge (*Cyperus rotundus*), yellow nutsedge (*Cyperus esculentus*)

Furthermore, some of the present compounds exhibit no significant phytotoxicity on the main crops such as corn (*Zea mays*), wheat (*Triticum aestivum*), barley (*Hordeum vulgare*), rice (*Oryza sativa*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*), and canola (*Brassica napus*); horticultural crops such as flowers and ornamental plants; and vegetable crops.

The present compounds can also attain the effective control of various weeds which may cause some trouble in the no-tillage cultivation of soybean (*Glycine max*), corn (*Zea mays*), wheat (*Triticum aestivum*), and other crops. Furthermore, some of the present compounds exhibit no significant phytotoxicity on the crops.

The present compounds also have herbicidal activity against various weeds which may cause some trouble in the flooding treatment on paddy fields, such as listed below.

Graminaceous weeds:

barnyardgrass (*Echinochloa oryzicola*)

Scrophulariaceous weeds:

common falsepimpernel (*Lindernia procumbens*)

Lythraceous weeds:

Indian toothcup (*Rotala indica*), red stem (*Ammannia multiflora*)

Elatinaceous weeds:

waterwort (*Elatine triandra*)

Cyperaceous weeds:

smallflower umbrella sedge (*Cyperus difformis*), hardstem bulrush (*Scirpus juncoides*), needle spikerush (*Eleocharis acicularis*), water nutgrass (*Cyperus serotinus*), water chestnut (*Eleocharis kuroguwai*)

Pontederiaceous weeds:

monochoria (*Monochoria vaginalis*)

Alismataceous weeds:

arrowhead (*Sagittaria pygmaea*), arrowhead (*Sagittaria trifolia*), waterplantain (*Alisma canaliculatum*)

Potamogetonaceous weeds:

roundleaf pondweed (*Potamogeton distinctus*)

Umbelloferous weeds:

watercelery sp. (*Oenanthe javanica*).

Furthermore, some of the present compounds exhibit no significant phytotoxicity on transplanted paddy rice.

The present compounds can also attain the control of a wide variety of weeds which are growing or will grow in the orchards, grasslands, lawns, forests, waterways, canals, or other non-cultivated lands.

The present compounds also have herbicidal activity against various aquatic weeds, such as water hyacinth (*Eichhornia crassipes*), which are growing or will grow at the waterside such as waterways or canals.

The present compounds have substantially the same characteristics as those of the herbicidal compounds disclosed in the published specification of International Patent Application, WO95/34659 corresponding to U.S. Pat. No. 5,767,373. In the case where crops with tolerance imparted by introducing a herbicide tolerance gene described in the published specification are cultivated, the present compounds can be used at larger rates than those used when ordinary crops without tolerance are cultivated, which makes it possible to control other unfavorable weeds more effectively.

When the present compounds are used as the active ingredients of herbicides, they are usually mixed with solid or liquid carriers or diluents, surfactants, and other auxiliary agents to give emulsifiable concentrates, wettable powders, flowables, granules, concentrated emulsions, water-dispersible granules, or other formulations.

These formulations may contain any of the present compounds as an active ingredient at an amount of 0.001 to 80% by weight, preferably 0.005 to 70% by weight, based on the total weight of the formulation.

The solid carrier or diluent which can be used may include, for example, fine powders or granules of the following materials: mineral matters such as kaolin clay, attapulgite clay, bentonite, acid clay, pyrophyllite, talc, diatomaceous earth, and calcite; organic substances such as walnut shell powder; water-soluble organic substances such as urea; inorganic salts such as ammonium sulfate; and synthetic hydrated silicon oxide. The liquid carrier or diluent which can be used may include, for example, aromatic hydrocarbons such as methylnaphthalene, phenylxylylethane, and alkylbenzene (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cottonseed oil; dimethylsulfoxide, N,N-dimethylformamide, acetonitrile, N-methylpyrrolidone, and water.

The surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

The auxiliary agent may include lignin sulfonates, alginates, polyvinyl alcohol, gum arabic, CMC (carboxymethylcellulose), and PAP (isopropyl acid phosphate).

The present compounds are usually formulated as described above and then used for pre- or post-emergence soil, foliar, or flooding treatment of weeds. The soil treatment may include soil surface treatment and soil incorporation. The foliar treatment may include application over the plants and directed application in which a chemical is applied only to weeds so as to keep off the crop plants.

The present compounds may often exhibit the enhancement of herbicidal activity when used in admixture with other herbicides. They can also be used in admixture with insecticides, acaricides, nematocides, fungicides, bactericides, plant growth regulators, fertilizers, and soil conditioners.

Examples of the herbicide which can be used in admixture with the present compounds are atrazin, cyanazine, dimethametryn, metribuzin, prometryn, simazine, simetryn, chlorotoluron, diuron, dymrone, fluometuron, isoproturon, linuron, methabenzthiazuron, bromoxynil, ioxynil, ethalfluralin, pendimethalin, trifluralin, acifluorfen, acifluorfen-sodium, bifenox, chlomethoxynil, fomesafen, lactofen, oxadiazon, oxadiargyl, oxyfluorfen, carfentrazon-ethyl, flumiclorac-pentyl, flumioxazine, fluthiacet-methyl, sulfentrazone, thidiazmin, azafenidin, pyraflufen-ethyl, difenzoquat, diquat, paraquat, 2,4-D, 2,4-DB, DCPA, MCPA, MCPB, clomeprop, clopyralid, dicamba, dithiopyr, fluroxypyr, mecoprop, naproanilide, phenothiol, quinclorac, triclopyr, thiazopyr, acetochlor, alachlor, butachlor, diethatyl-ethyl, metolachlor, pretilachlor, propachlor, bensulfuron-methyl, chlorsulfuron, chlorimuron-ethyl, halosulfuron-methyl, metsulfuron-methyl, nicosulfuron, primisulfuron-methyl, pyrazosulfuron-ethyl, sulfometuron-methyl, thifensulfuron-methyl, triasulfuron, tribenuron-methyl, oxasulfuron, azimsulfuron, cloransulam-methyl, cyclosulfamuron, flumetsulam, flupyrsulfuron, flazasulfuron, imazosulfron, metosulam, diclosulam, prosulfuron, rimsulfuron, triflusulfuron-methyl, ethoxysulfuron, sulfosulfuron, imazamethabenzmethyl, imazapyr, imazaquin, imazethapyr, imazameth, imazamox, bispyribac-sodium, pyriminobac-methyl, pyrithiobac-sodium, alloxydim-sodium, clethodim, sethoxydim, tralkoxydim, dichlofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, benzofenap, clomazone, diflufenican, norflurazon, pyrazolate, pyrazoxyfen, flurtamone, isoxaflutole, sulcotrione, glufosinate-ammonium, glyphosate, bentazon, benthiocarb, bromobutide, butamifos, butylate, dimepiperate, dimethenamid, DSMA, EPTC, esprocarb, isoxaben, mefenacet, molinate, MSMA, piperophos, pyributicarb, propanil, pyridate, triallate, cafenstrol, flupoxam, fluthiamride, diflufenzopyr, triaziflam, pentoxazone, epoprodam, metobenzuron, and oxaziclomefone.

The above compounds are described in the catalog of Farm Chemicals Handbook, 1995 (published by Meister Publishing Company); AG CHEM NEW COMPOUND REVIEW, VOL. 13 or 15, 1995 (published by AG CHEM INFORMATION SERVICES); "Josouzai Kenkyu Souran" (published by Hakuyu-sha); or HERBICIDE HANDBOOK, Seventh Edition (published by Weed Science Society of America).

The following will describe some particular examples of the above admixture, in which the present compounds are designated by their compound numbers shown in Table 1 below.

1. A compound selected from the group consisting of the present compounds 268, 269, 271, 272, 274, 291, 294, 295, and 327 is mixed with a compound selected from the group consisting of atrazin, cyanazine, dicamba, flumetsulam, halosulfuron-methyl, and isoxaflutole at a weight ratio of 1:0.05 to 1000.
2. A compound selected from the group consisting of the present compounds 268, 269, 271, 272, 274, 291, 294, 295, and 327 is mixed with a compound selected from the group consisting of metolachlor, acetochlor, dimethenamid, pendimethalin, and fluthiamid at a weight ratio of 1:0.1 to 1000.
3. A compound selected from the group consisting of the present compounds 268, 269, 271, 272, 274, 291, 294, 295, and 327 is mixed with a compound selected from the group consisting of cotoran, diuron, and norlurazon at a weight ratio of 1:0.05 to 1000.
4. A compound selected from the group consisting of the present compounds 268, 269, 271, 272, 274, 291, 294, 295, and 327 is mixed with a compound selected from the group consisting of isoproturon and chlorotoluron at a weight ratio of 1:0.1 to 1000.

5. A compound selected from the group consisting of the present compounds 268, 269, 271, 272, 274, 291, 294, 295, and 327 is mixed with a compound selected from the group consisting of mecoprop, fluroxypyr, 2,4-D, bromoxynil, and joxynil at a weight ratio of 1:0.05 to 1000.

6. A compound selected from the group consisting of the present compounds 268, 269, 271, 272, 274, 291, 294, 295, and 327 is mixed with a compound selected from the group consisting of diflufenican, metsulfuronmethyl, fenoxaprop-ethyl, carfentrazon, flupyrsulfuon, and clodinafoppropargyl at a weight ratio of 1:0.001 to 100.

When the present compounds are used as the active ingredients of herbicides, the application amount, although it may vary with the weather conditions, formulation types, application times, application methods, soil conditions, crops to be protected, weeds to be controlled, and other factors, is usually in the range of 0.01 to 10,000 g, preferably 1 to 8000 g, per hectare. In the case of emulsifiable concentrates, wettable powders, flowables, concentrated emulsions, water-dispersible granules, or other similar formulations, they are usually applied after diluted in their prescribed amounts with water (if necessary, containing an adjuvant such as a spreading agent) at a ratio of 10 to 1000 liters per hectare. In the case of granules or some types of flowables, they are usually applied as such without any dilution.

The adjuvant which can be used, if necessary, may include, in addition to the surfactants as described above, polyoxyethylene resin acids (esters), lignin sulfonates, abietates, dinaphthylmethanedisulfonates, crop oil concentrates, and vegetable oils such as soybean oil, corn oil, cottonseed soil, and sunflower oil.

The present compounds can also be used as the active ingredients of harvesting aids such as defoliants and desiccants for cotton (Gossipyum spp.), and desiccants for potato (*Solanum tuberosum*). In these cases, the present compounds are usually formulated in the same manner as the case where they are used as the active ingredients of herbicides, and used alone or in admixture with other harvesting aids for foliar treatment before the harvesting of crops.

EXAMPLES

The present invention will be further illustrated by the following production examples, formulation examples, and test examples; however, the present invention is not limited to these examples.

The following will describe production examples for the present compounds and their production intermediates.

Production Example 1

First, 400 mg (1.2 mmol) of 2-(4-chloro-2-fluoro-5-hydroxyphenyl)-4-methyl-5-trifluoromethyl-3-oxo-2,3-dihydropyridazine (hereinafter referred to as intermediate 1; produced in the Reference Production Example described below) was dissolved in 2.0 ml of N,N-dimethylformamide, to which 257 mg (1.86 mmol) of potassium carbonate and 286 mg (1.36 mmol) of methyl 4-bromocrotonate, and the mixture was stirred at room temperature for 3 hours. The reaction mixture was poured into water, and extracted with ethyl acetate. The organic layer was washed with saturated aqueous sodium chloride solution, dried over anhydrous magnesium sulfate, and then concentrated. The residue was subjected to silica gel column chromatography, which afforded 194 mg (0.46 mmol) of 2-{4-chloro-2-fluoro-5-(E-3-methoxycarbonyl-2-propenyloxy)phenyl}-4-methyl-5-trifluoromethyl-3-oxo-2,3-dihydropyridazine (present compound 327), m.p. 153.2° C.

Production Example 2

First, 300 mg (0.93 mmol) of 2-(4-chloro-2-fluoro-5-hydroxyphenyl)-4-methyl-5-trifluoromethyl-3-oxo-2,3-dihydropyridazine (intermediate 1) was dissolved in 1.5 ml of N,N-dimethylformamide, to which 193 mg (1.39 mmol) of potassium carbonate, 181 mg (1.02 mmol) of (bromomethyl)cyclohexane, and 154 mg (0.93 mmol) of potassium iodide were added, and the mixture was stirred at 60° C. for 2 hours. The reaction mixture was poured into water, and extracted with ethyl acetate. The organic layer was washed with saturated aqueous sodium chloride solution, dried over anhydrous magnesium sulfate, and then concentrated. The residue was subjected to silica gel column chromatography, which afforded 26 mg (0.062 mmol) of 2-(4-chloro-2-fluoro-5-cyclohexylmethyloxyphenyl)-4-methyl-5-trifluoromethyl-3-oxo-2,3-dihydropyridazine (present compound 271), m.p. 90.2° C.

Production Example 3

First, 400 mg (1.2 mmol) of 2-(4-chloro-2-fluoro-5-hydroxyphenyl)-4-methyl-5-trifluoromethyl-3-oxo-2,3-dihydropyridazine (intermediate 1) was dissolved in 2.0 ml of N,N-dimethylformamide, to which 257 mg (1.86 mmol) of potassium carbonate, 220 mg (1.48 mmol) of (bromomethyl)cyclobutane, and 226 mg (1.36 mmol) of potassium iodide were added, and the mixture was stirred at 60° C. for 1 hour. The reaction mixture was poured into water, and extracted with ethyl acetate. The organic layer was washed with saturated aqueous sodium chloride solution, dried over anhydrous magnesium sulfate, and then concentrated. The residue was subjected to silica gel column chromatography, which afforded 66 mg (0.17 mmol) of 2-(4-chloro-2-fluoro-5-cyclobutylmethyloxyphenyl)-4-methyl-5-trifluoromethyl-3-oxo-2,3-dihydropyridazine (present compound 269), m.p. 85.3° C.

Production Example 4

First, 400 mg (1.2 mmol) of 2-(4-chloro-2-fluoro-5-hydroxyphenyl)-4-methyl-5-trifluoromethyl-3-oxo-2,3-dihydropyridazine (intermediate 1) was dissolved in 2.0 ml of N,N-dimethylformamide, to which 257 mg (1.86 mmol) of potassium carbonate, 200 mg (1.48 mmol) of (bromomethyl)cyclopropane, and 246 mg (1.48 mmol) of potassium iodide were added, and the mixture was stirred at 60° C. for 1 hour. The reaction mixture was poured into water, and extracted with ethyl acetate. The organic layer was washed with saturated aqueous sodium chloride solution, dried over anhydrous magnesium sulfate, and then concentrated. The residue was subjected to silica gel column chromatography, which afforded 115 mg (0.31 mmol) of 2-(4-chloro-2-fluoro-5-cyclopropylmethyloxyphenyl)-4-methyl-5-trifluoromethyl-3-oxo-2,3-dihydropyridazine (present compound 268), m.p. 82.3° C.

Production Example 5

First, 400 mg (1.2 mmol) of 2-(4-chloro-2-fluoro-5-hydroxyphenyl)-4-methyl-5-trifluoromethyl-3-oxo-2,3-dihydropyridazine (intermediate 1) was dissolved in 2.0 ml of N,N-dimethylformamide, to which 257 mg (1.86 mmol) of potassium carbonate and 165 mg (1.36 mmol) of allyl bromide were added, and the mixture was stirred at room temperature for 30 minutes. The reaction mixture was poured into water, and extracted with ethyl acetate. The organic layer was washed with saturated aqueous sodium chloride solution, dried over anhydrous magnesium sulfate, and then concentrated. The residue was subjected to silica gel column chromatography, which afforded 405 mg (1.1 mmol) of 2-{4-chloro-2-fluoro-5-(2-propenyloxy)phenyl}-4-methyl-5-trifluoromethyl-3-oxo-2,3-dihydropyridazine (hereinafter referred to as intermediate 2), m.p. 79.8° C.

Then, 182 mg (0.50 mmol) of intermediate 2 was dissolved in 5.0 ml of methylene chloride, to which 1.5 ml of 0.2 N aqueous sodium hydrogencarbonate solution and 123 mg of m-chloroperbenzoic acid were added, and the mixture was stirred at room temperature for 3 hours. After completion of the reaction, the reaction mixture was extracted with chloroform. The organic layer was dried over anhydrous magnesium sulfate, and then concentrated. The residue was subjected to silica gel column chromatography, which afforded 51 mg (0.13 mmol) of 2-{4-chloro-2-fluoro-5-(2,3-epoxypropyloxy)phenyl}-4-methyl-5-trifluoromethyl-3-oxo-2,3-dihydropyridazine (present compound 274), m.p. 127.2° C.

Production Example 6

To a mixture of 363 mg (1.0 mmol) of 2-{4-chloro-2-fluoro-5-(2-propenyloxy)phenyl}-4-methyl-5-trifluoromethyl-3-oxo-2,3-dihydropyridazine (intermediate 2), 1.2 ml of tetrahydrofuran, 0.25 ml of water, and 137 mg (0.01 mmol) of 1.85% aqueous osmium tetraoxide solution was added 428 mg (2.0 mmol) of sodium periodate at 0° C. over 10 minutes. The mixture was stirred for 30 minutes, warmed to room temperature, and then stirred for 1.5 hours. The reaction mixture was filtered thorough Celite, and the residue was washed with ethyl acetate. The filtrate and the ethyl acetate were combined, and the mixture was washed with water and saturated aqueous sodium chloride solution in this order, dried over anhydrous magnesium sulfate, and then concentrated. The residue was subjected to silica gel column chromatography, which afforded 155 mg (0.43 mmol) of 2-(4-chloro-2-fluoro-5-formylmethoxyphenyl)-4-methyl-5-trifluoromethyl-3-oxo-2,3-dihydropyridazine (present compound 272), m.p. 107.1° C.

Production Example 7

A mixture of 180 mg (0.49 mmol) of 2-(4-chloro-2-fluoro-5-formylmethoxyphenyl)-4-methyl-5-trifluoromethyl-3-oxo-2,3-dihydropyridazine (present compound 272), 2.3 mg (0.012 mmol) of p-toluenesulfonic acid monohydrate, 398 mg (3.8 mmol) of trimethyl orthoformate, and 0.41 mg of methanol was stirred at room temperature for 1 hour. The reaction mixture was neutralized by the addition of a saturated aqueous sodium hydrogencarbonate solution, and extracted with chloroform. The organic layer was dried over anhydrous magnesium sulfate, and then concentrated. The residue was subjected to silica gel column chromatography, which afforded 99 mg (0.24 mmol) of 2-{4-chloro-2-fluoro-5-(2,2-dimethoxyethyloxy)phenyl}-4-methyl-5-trifluoromethyl-3-oxo-2,3-dihydropyridazine (present compound 291), m.p. 86.0° C.

Production Example 8

A mixture of 180 mg (0.49 mmol) of 2-(4-chloro-2-fluoro-5-formylmethoxyphenyl)-4-methyl-5-trifluoromethyl-3-oxo-2,3-dihydropyridazine (present compound 272), 1.8 mg (0.0093 mmol) of p-toluenesulfonic acid monohydrate, 73 mg (0.49 mmol) of triethyl orthoformate, and 0.32 g of ethylene glycol was stirred at 60° C. for 3 hours. The reaction mixture was returned to room temperature, and then neutralized by the addition of a saturated aqueous sodium hydrogencarbonate solution, and extracted with chloroform. The organic layer was dried over anhydrous magnesium sulfate, and then concentrated. The residue was subjected to silica gel column chromatography, which afforded 79 mg (0.19 mmol) of 2-(4-chloro-2-fluoro-5-(2,5-dioxoranylethyloxy)phenyl)-4-methyl-5-trifluoromethyl-3-oxo-2,3-dihydropyridazine (present compound 294).

$^1$H-NMR (300 MHz, CDCl$_3$, TMS) δ (ppm): 2.42 (3H, q, J=1.7 Hz), 3.9–4.0 (2H, m), 4.0–4.1 (4H, m), 5.33 (1H, t, J=3.4 Hz), 7.03 (1H, d, J=6.3 Hz), 7.31 (1H, d, J=9.0 Hz), 8.00 (1H, s).

Production Example 9

A mixture of 180 mg (0.49 mmol) of 2-(4-chloro-2-fluoro-5-formylmethoxyphenyl)-4-methyl-5-trifluoromethyl-3-oxo-2,3-dihydropyridazine (present compound 272), 1.8 mg (0.0093 mmol) of p-toluenesulfonic acid monohydrate, 73 mg (0.49 mmol) of triethyl orthoformate, and 0.39 g of trimethylene glycol was stirred at 60° C. for 3 hours. The reaction mixture was returned to room temperature, and then neutralized by the addition of a saturated aqueous sodium hydrogencarbonate solution, and extracted with chloroform. The organic layer was dried over anhydrous magnesium sulfate, and then concentrated. The residue was subjected to silica gel column chromatography, which afforded 163 mg (0.39 mmol) of 2-(4-chloro-2-fluoro-5-(2,6-dioxanylethyloxy)phenyl)-4-methyl-5-trifluoromethyl-3-oxo-2,3-dihydropyridazine (present compound 295), m.p. 112.4° C.

Some examples of the present compounds are shown by the definition of each substituent in the compounds of general formula (1), together with their compound numbers in Table 1. In this table, "n", "i", and "c" represent normal-, iso-, and cyclo-, respectively, and "(O)" means that the oxygen atom, together with the adjacent two carbon atoms, forms an epoxide.

TABLE 1

| Compound No. | X | Y | Z$^1$ | R$^1$ | R$^2$ | R$^3$ | R$^4$ | R$^5$ | R$^6$ or R$^6$–R$^7$ |
|---|---|---|---|---|---|---|---|---|---|
| 1 | H | Cl | O | CF$_3$ | H | H | H | cC$_3$H$_5$ | |
| 2 | H | Cl | O | CF$_3$ | H | H | H | cC$_4$H$_7$ | |
| 3 | H | Cl | O | CF$_3$ | H | H | H | cC$_5$H$_9$ | |
| 4 | H | Cl | O | CF$_3$ | H | H | H | cC$_6$H$_{11}$ | |
| 5 | H | Cl | O | CF$_3$ | H | H | H | CHO | |
| 6 | H | Cl | O | CF$_3$ | H | H | H | CH$_2$C$_6$H$_5$ | |
| 7 | H | Cl | O | CF$_3$ | H | H | H | CH(O)CH$_2$ | |

TABLE 1-continued

| Compound No. | X | Y | $Z^1$ | $R^1$ | $R^2$ | $R^3$ | $R^4$ | $R^5$ | $R^6$ or $R^6$–$R^7$ |
|---|---|---|---|---|---|---|---|---|---|
| 8 | H | Cl | O | $CF_3$ | H | H | H | $CH(O)CHCH_3$ | |
| 9 | H | Cl | O | $CF_3$ | H | H | H | $CH_2CH(O)CH_2$ | |
| 10 | H | Cl | O | $CF_3$ | H | H | H | $CH_2CH_2CH(O)CH_2$ | |
| 11 | H | Cl | O | $CF_3$ | H | H | H | $CH_2cC_3H_5$ | |
| 12 | H | Cl | O | $CF_3$ | H | H | H | $(CH_2)_2cC_3H_5$ | |
| 13 | H | Cl | O | $CF_3$ | H | H | H | $CH_2cC_4H_7$ | |
| 14 | H | Cl | O | $CF_3$ | H | H | H | $CH_2cC_6H_{11}$ | |
| 15 | H | Cl | O | $CF_3$ | H | H | H | $CH_2CHO$ | |
| 16 | H | Cl | O | $CF_3$ | H | H | H | $(CH_2)_2CHO$ | |
| 17 | H | Cl | O | $CF_3$ | H | H | H | $(CH_2)_3CHO$ | |
| 18 | H | Cl | O | $CF_3$ | H | H | H | $CH(CH_3)CHO$ | |
| 19 | H | Cl | O | $CF_3$ | H | H | H | $CH=CHcC_3H_5$ | |
| 20 | H | Cl | O | $CF_3$ | H | H | H | $CH=CHCH_2cC_3H_5$ | |
| 21 | H | ClI | O | $CF_3$ | H | H | H | $CH=CHCH_2cC_4H_7$ | |
| 22 | H | Cl | O | $CF_3$ | H | H | H | $CH=CHCHO$ | |
| 23 | H | Cl | O | $CF_3$ | H | H | H | $CH=C(CH_3)CHO$ | |
| 24 | H | Cl | O | $CF_3$ | H | H | H | $CH(OR^6)_2$ | $CH_3$ |
| 25 | H | Cl | O | $CF_3$ | H | H | H | $CH(OR^6)_2$ | $C_2H_5$ |
| 26 | H | Cl | O | $CF_3$ | H | H | H | $CH(OR^6)_2$ | $nC_3H_7$ |
| 27 | H | Cl | O | $CF_3$ | H | H | H | $CH(OR^6)(OR^7)$ | $(CH_2)_2$ |
| 28 | H | Cl | O | $CF_3$ | H | H | H | $CH(OR^6)(OR^7)$ | $(CH_2)_3$ |
| 29 | H | Cl | O | $CF_3$ | H | H | H | $CH(OR^6)(OR^7)$ | $(CH_2)_4$ |
| 30 | H | Cl | O | $CF_3$ | H | H | H | $CH_2CH(OR^6)_2$ | $CH_3$ |
| 31 | H | Cl | O | $CF_3$ | H | H | H | $CH_2CH(OR^6)_2$ | $C_2H_5$ |
| 32 | H | Cl | O | $CF_3$ | H | H | H | $CH_2CH(OR^6)(OR^7)$ | $(CH_2)_2$ |
| 33 | H | Cl | O | $CF_3$ | H | H | H | $CH_2CH(OR^6)(OR^7)$ | $(CH_2)_3$ |
| 34 | H | Cl | O | $CF_3$ | H | H | H | $CH_2CH_2CH(OR^6)_2$ | $CH_3$ |
| 35 | H | Cl | O | $CF_3$ | H | H | H | $CH_2CH_2CH(OR^6)_2$ | $C_2H_5$ |
| 36 | H | Cl | O | $CF_3$ | H | H | H | $CH_2CH_2CH(OR^6)(OR^7)$ | $(CH_2)_2$ |
| 37 | H | Cl | O | $CF_3$ | H | H | H | $CH_2CH_2CH(OR^6)(OR^7)$ | $(CH_2)_3$ |
| 38 | H | Cl | O | $CF_3$ | H | H | H | $CH=CHCH(OR^6)_2$ | $CH_3$ |
| 39 | H | Cl | O | $CF_3$ | H | H | H | $CH=CHCH(OR^6)_2$ | $C_2H_5$ |
| 40 | H | Cl | O | $CF_3$ | H | H | H | $CH(CH_3)CH(OR^6)_2$ | $CH_3$ |
| 41 | H | Cl | O | $CF_3$ | H | H | H | $CH(CH_3)CH(OR^6)(OR^7)$ | $(CH_2)_2$ |
| 42 | H | Cl | O | $CF_3$ | H | H | H | $CH(SR^6)_2$ | $CH_3$ |
| 43 | H | Cl | O | $CF_3$ | H | H | H | $CH(SR^6)_2$ | $C_2H_5$ |
| 44 | H | Cl | O | $CF_3$ | H | H | H | $CH(SR^6)_2$ | $nC_3H_7$ |
| 45 | H | Cl | O | $CF_3$ | H | H | H | $CH(SR^6)(SR^7)$ | $(CH_2)_2$ |
| 46 | H | Cl | O | $CF_3$ | H | H | H | $CH(SR^6)(SR^7)$ | $(CH_2)_3$ |
| 47 | H | Cl | O | $CF_3$ | H | H | H | $CH(SR^6)(SR^7)$ | $(CH_2)_4$ |
| 48 | H | Cl | O | $CF_3$ | H | H | H | $CH_2CH(SR^6)_2$ | $CH_3$ |
| 49 | H | Cl | O | $CF_3$ | H | H | H | $CH_2CH(SR^6)_2$ | $C_2H_5$ |
| 50 | H | Cl | O | $CF_3$ | H | H | H | $CH_2CH(SR^6)(SR^7)$ | $(CH_2)_2$ |
| 51 | H | Cl | O | $CF_3$ | H | H | H | $CH_2CH(SR^6)(SR^7)$ | $(CH_2)_3$ |
| 52 | H | Cl | O | $CF_3$ | H | H | H | $CH_2CH_2CH(SR^6)_2$ | $CH_3$ |
| 53 | H | Cl | O | $CF_3$ | H | H | H | $CH_2CH_2CH(SR^6)_2$ | $C_2H_5$ |
| 54 | H | Cl | O | $CF_3$ | H | H | H | $CH_2CH_2CH(SR^6)(SR^7)$ | $(CH_2)_2$ |
| 55 | H | Cl | O | $CF_3$ | H | H | H | $CH_2CH_2CH(SR^6)(SR^7)$ | $(CH_2)_3$ |
| 56 | H | Cl | O | $CF_3$ | H | H | H | $CH=CHCH(SR^6)_2$ | $CH_3$ |
| 57 | H | Cl | O | $CF_3$ | H | H | H | $CH=CHCH(SR^6)_3$ | $C_2H_5$ |
| 58 | H | Cl | O | $CF_3$ | H | H | H | $CH=CHCOOH$ | |
| 59 | H | Cl | O | $CF_3$ | H | H | H | $CH=C(CH_3)COOH$ | |
| 60 | H | Cl | O | $CF_3$ | H | H | H | $CH=CHCOOCH_3$ | |
| 61 | H | Cl | O | $CF_3$ | H | H | H | $CH=CHCOOC_2H_5$ | |
| 62 | H | Cl | O | $CF_3$ | H | H | H | $CH=CHCOOnC_3H_7$ | |
| 63 | H | Cl | O | $CF_3$ | H | H | H | $CH=CHCOOiC_3H_7$ | |
| 64 | H | Cl | O | $CF_3$ | H | H | H | $CH=C(CH_3)COOCH_3$ | |
| 65 | H | Cl | O | $CF_3$ | H | H | H | $CH=C(CH_3)COOC_2H_5$ | |
| 66 | H | Cl | O | $CF_3$ | H | H | H | $CH=C(CH_3)COOnC_3H_7$ | |
| 67 | H | Cl | O | $CF_3$ | H | H | H | $CH=C(CH_3)COOiC_3H_7$ | |
| 68 | H | Cl | O | $CF_3$ | H | H | H | $CH=CHCOOCH_2CH_2Cl$ | |
| 69 | H | Cl | O | $CF_3$ | H | H | H | $CH=CHCOOCH_2OCH_3$ | |
| 70 | H | Cl | O | $CF_3$ | H | H | H | $CH=C(CH_3)COOCH_2OCH_3$ | |
| 71 | H | Cl | O | $CF_3$ | H | H | H | $CH=CHCOOcC_3H_5$ | |
| 72 | H | Cl | O | $CF_3$ | H | H | H | $CH=CHCOOcC_4H_7$ | |
| 73 | H | Cl | O | $CF_3$ | H | H | H | $CH=CHCOOcC_5H_9$ | |
| 74 | H | Cl | O | $CF_3$ | H | H | H | $CH=C(CH_3)COOcC_3H_5$ | |
| 75 | H | Cl | O | $CF_3$ | H | H | H | $CH=C(CH_3)COOcC_4H_7$ | |
| 76 | H | Cl | O | $CF_3$ | H | H | H | $CH=C(CH_3)COOcC_5H_9$ | |
| 77 | H | Cl | O | $CF_3$ | H | H | H | $CH=CHCOCH_3$ | |
| 78 | H | Cl | O | $CF_3$ | H | H | H | $CH=CHCOC_2H_5$ | |
| 79 | H | Cl | O | $CF_3$ | H | H | H | $CH=C(CH_3)COCH_3$ | |
| 80 | H | Cl | O | $CF_3$ | H | H | H | $CH=CHCOCH_2Cl$ | |
| 81 | H | Cl | O | $CF_3$ | H | H | H | $CH=CHCOCH_2CH_2OCH_3$ | |
| 82 | H | Cl | O | $CF_3$ | H | H | H | $CH=CHCOcC_3H_5$ | |
| 83 | H | Cl | O | $CF_3$ | H | H | H | $CH=CHCOcC_4H_7$ | |

TABLE 1-continued

| Compound No. | X | Y | Z¹ | R¹ | R² | R³ | R⁴ | R⁵ | R⁶ or R⁶–R⁷ |
|---|---|---|---|---|---|---|---|---|---|
| 84 | H | Cl | O | $CF_3$ | H | H | H | $CH{=}CHOcC_5H_9$ | |
| 85 | H | Cl | O | $CF_3$ | H | H | H | $CH{=}CHOcC_6H_{11}$ | |
| 86 | H | Cl | O | $CF_3$ | H | H | H | $CH{=}C(CH_3)COcC_5H_9$ | |
| 87 | H | Cl | O | $CF_3$ | H | H | H | $CH{=}C(CH_3)COcC_6H_{11}$ | |
| 88 | H | Cl | O | $CF_3$ | H | H | $CH_3$ | $CH{=}CHCOOCH_3$ | |
| 89 | H | Cl | O | $CF_3$ | H | H | $CH_3$ | $CH{=}CHCOOC_2H_5$ | |
| 90 | H | Cl | O | $CF_3$ | $CH_3$ | H | H | $cC_3H_5$ | |
| 91 | H | Cl | O | $CF_3$ | $CH_3$ | H | H | $cC_4H_7$ | |
| 92 | H | Cl | O | $CF_3$ | $CH_3$ | H | H | $cC_5H_9$ | |
| 93 | H | Cl | O | $CF_3$ | $CH_3$ | H | H | $cC_6H_{11}$ | |
| 94 | H | Cl | O | $CF_3$ | $CH_3$ | H | H | CHO | |
| 95 | H | Cl | O | $CF_3$ | $CH_3$ | H | H | $CH_2C_6H_5$ | |
| 96 | H | Cl | O | $CF_3$ | $CH_3$ | H | H | $CH(O)CH_2$ | |
| 97 | H | Cl | O | $CF_3$ | $CH_3$ | H | H | $CH(O)CHCH_3$ | |
| 98 | H | Cl | O | $CF_3$ | $CH_3$ | H | H | $CH_2CH(O)CH_2$ | |
| 99 | H | Cl | O | $CF_3$ | $CH_3$ | H | H | $CH_2CH_2CH(O)CH_2$ | |
| 100 | H | Cl | O | $CF_3$ | $CH_3$ | H | H | $CH_2cC_3H_5$ | |
| 101 | H | Cl | O | $CF_3$ | $CH_3$ | H | H | $(CH_2)_2cC_3H_5$ | |
| 102 | H | Cl | O | $CF_3$ | $CH_3$ | H | H | $CH_2cC_4H_7$ | |
| 103 | H | Cl | O | $CF_3$ | $CH_3$ | H | H | $CH_2cC_6H_{11}$ | |
| 104 | H | Cl | O | $CF_3$ | $CH_3$ | H | H | $CH_2CHO$ | |
| 105 | H | Cl | O | $CF_3$ | $CH_3$ | H | H | $(CH_2)_2CHO$ | |
| 106 | H | Cl | O | $CF_3$ | $CH_3$ | H | H | $(CH_2)_3CHO$ | |
| 107 | H | Cl | O | $CF_3$ | $CH_3$ | H | H | $CH(CH_3)CHO$ | |
| 108 | H | Cl | O | $CF_3$ | $CH_3$ | H | H | $CH{=}CHcC_3H_5$ | |
| 109 | H | Cl | O | $CF_3$ | $CH_3$ | H | H | $CH{=}CHCH_2cC_3H_5$ | |
| 110 | H | Cl | O | $CF_3$ | $CH_3$ | H | H | $CH{=}CHCH_2cC_4H_7$ | |
| 111 | H | Cl | O | $CF_3$ | $CH_3$ | H | H | $CH{=}CHCHO$ | |
| 112 | H | Cl | O | $CF_3$ | $CH_3$ | H | H | $CH{=}C(CH_3)CHO$ | |
| 113 | H | Cl | O | $CF_3$ | $CH_3$ | H | H | $CH(OR^6)_2$ | $CH_3$ |
| 114 | H | Cl | O | $CF_3$ | $CH_3$ | H | H | $CH(OR^6)_2$ | $C_2H_5$ |
| 115 | H | Cl | O | $CF_3$ | $CH_3$ | H | H | $CH(OR^6)_2$ | $nC_3H_7$ |
| 116 | H | Cl | O | $CF_3$ | $CH_3$ | H | H | $CH(OR^6)(OR^7)$ | $(CH_2)_2$ |
| 117 | H | Cl | O | $CF_3$ | $CH_3$ | H | H | $CH(OR^6)(OR^7)$ | $(CH_2)_3$ |
| 118 | H | Cl | O | $CF_3$ | $CH_3$ | H | H | $CH(OR^6)(OR^7)$ | $(CH_2)_4$ |
| 119 | H | Cl | O | $CF_3$ | $CH_3$ | H | H | $CH_2CH(OR^6)_2$ | $CH_3$ |
| 120 | H | Cl | O | $CF_3$ | $CH_3$ | H | H | $CH_2CH(OR^6)_2$ | $C_2H_5$ |
| 121 | H | Cl | O | $CF_3$ | $CH_3$ | H | H | $CH_2CH(OR^6)(OR^7)$ | $(CH_2)_2$ |
| 122 | H | Cl | O | $CF_3$ | $CH_3$ | H | H | $CH_2CH(OR^6)(OR^7)$ | $(CH_2)_3$ |
| 123 | H | Cl | O | $CF_3$ | $CH_3$ | H | H | $CH_2CH_2CH(OR^6)_2$ | $CH_3$ |
| 124 | H | Cl | O | $CF_3$ | $CH_3$ | H | H | $CH_2CH_2CH(OR^6)_2$ | $C_2H_5$ |
| 125 | H | Cl | O | $CF_3$ | $CH_3$ | H | H | $CH_2CH_2CH(OR^6)(OR^7)$ | $(CH_2)_2$ |
| 126 | H | Cl | O | $CF_3$ | $CH_3$ | H | H | $CH_2CH_2CH(OR^6)(OR^7)$ | $(CH_2)_3$ |
| 127 | H | Cl | O | $CF_3$ | $CH_3$ | H | H | $CH{=}CHCH(OR^6)_2$ | $CH_3$ |
| 128 | H | Cl | O | $CF_3$ | $CH_3$ | H | H | $CH{=}CHCH(OR^6)_2$ | $C_2H_5$ |
| 129 | H | Cl | O | $CF_3$ | $CH_3$ | H | H | $CH(CH_3)CH(OR^6)_2$ | $CH_3$ |
| 130 | H | Cl | O | $CF_3$ | $CH_3$ | H | H | $CH(CH_3)CH(OR^6)(OR^7)$ | $(CH_2)_2$ |
| 131 | H | Cl | O | $CF_3$ | $CH_3$ | H | H | $CH(SR^6)_2$ | $CH_3$ |
| 132 | H | Cl | O | $CF_3$ | $CH_3$ | H | H | $CH(SR^6)_2$ | $C_2H_5$ |
| 133 | H | Cl | O | $CF_3$ | $CH_3$ | H | H | $CH(SR^6)_2$ | $nC_3H_7$ |
| 134 | H | Cl | O | $CF_3$ | $CH_3$ | H | H | $CH(SR^6)(SR^7)$ | $(CH_2)_2$ |
| 135 | H | Cl | O | $CF_3$ | $CH_3$ | H | H | $CH(SR^6)(SR^7)$ | $(CH_2)_3$ |
| 136 | H | Cl | O | $CF_3$ | $CH_3$ | H | H | $CH(SR^6)(SR^7)$ | $(CH_2)_4$ |
| 137 | H | Cl | O | $CF_3$ | $CH_3$ | H | H | $CH_2CH(SR^6)_2$ | $CH_3$ |
| 138 | H | Cl | O | $CF_3$ | $CH_3$ | H | H | $CH_2CH(SR^6)_2$ | $C_2H_5$ |
| 139 | H | Cl | O | $CF_3$ | $CH_3$ | H | H | $CH_2CH(SR^6)(SR^7)$ | $(CH_2)_2$ |
| 140 | H | Cl | O | $CF_3$ | $CH_3$ | H | H | $CH_2CH(SR^6)(SR^7)$ | $(CH_2)_3$ |
| 141 | H | Cl | O | $CF_3$ | $CH_3$ | H | H | $CH_2CH_2CH(SR^6)_2$ | $CH_3$ |
| 142 | H | Cl | O | $CF_3$ | $CH_3$ | H | H | $CH_2CH_2CH(SR^6)_2$ | $C_2H_5$ |
| 143 | H | Cl | O | $CF_3$ | $CH_3$ | H | H | $CH_2CH_2CH(SR^6)(SR^7)$ | $(CH_2)_2$ |
| 144 | H | Cl | O | $CF_3$ | $CH_3$ | H | H | $CH_2CH_2CH(SR^6)(SR^7)$ | $(CH_2)_3$ |
| 145 | H | Cl | O | $CF_3$ | $CH_3$ | H | H | $CH{=}CHCH(SR^6)_2$ | $CH_3$ |
| 146 | H | Cl | O | $CF_3$ | $CH_3$ | H | H | $CH{=}CHCH(SR^6)_3$ | $C_2H_5$ |
| 147 | H | Cl | O | $CF_3$ | $CH_3$ | H | H | $CH{=}CHCOOH$ | |
| 148 | H | Cl | O | $CF_3$ | $CH_3$ | H | H | $CH{=}C(CH_3)COOH$ | |
| 149 | H | Cl | O | $CF_3$ | $CH_3$ | H | H | $CH{=}CHCOOCH_3$ | |
| 150 | H | Cl | O | $CF_3$ | $CH_3$ | H | H | $CH{=}CHCOOC_2H_5$ | |
| 151 | H | Cl | O | $CF_3$ | $CH_3$ | H | H | $CH{=}CHCOOnC_3H_7$ | |
| 152 | H | Cl | O | $CF_3$ | $CH_3$ | H | H | $CH{=}CHCOOiC_3H_7$ | |
| 153 | H | Cl | O | $CF_3$ | $CH_3$ | H | H | $CH{=}C(CH_3)COOCH_3$ | |
| 154 | H | Cl | O | $CF_3$ | $CH_3$ | H | H | $CH{=}C(CH_3)COOC_2H_5$ | |
| 155 | H | Cl | O | $CF_3$ | $CH_3$ | H | H | $CH{=}C(CH_3)COOnC_3H_7$ | |
| 156 | H | Cl | O | $CF_3$ | $CH_3$ | H | H | $CH{=}C(CH_3)COOiC_3H_7$ | |
| 157 | H | Cl | O | $CF_3$ | $CH_3$ | H | H | $CH{=}CHCOOCH_2CH_2Cl$ | |
| 158 | H | Cl | O | $CF_3$ | $CH_3$ | H | H | $CH{=}CHCOOCH_2OCH_3$ | |
| 159 | H | Cl | O | $CF_3$ | $CH_3$ | H | H | $CH{=}C(CH_3)COOCH_2OCH_3$ | |

TABLE 1-continued

| Compound No. | X | Y | Z¹ | R¹ | R² | R³ | R⁴ | R⁵ | R⁶ or R⁶–R⁷ |
|---|---|---|---|---|---|---|---|---|---|
| 160 | H | Cl | O | $CF_3$ | $CH_3$ | H | H | $CH=CHCOOcC_3H_5$ | |
| 161 | H | Cl | O | $CF_3$ | $CH_3$ | H | H | $CH=CHCOOcC_4H_7$ | |
| 162 | H | Cl | O | $CF_3$ | $CH_3$ | H | H | $CH=CHCOOcC_5H_9$ | |
| 163 | H | Cl | O | $CF_3$ | $CH_3$ | H | H | $CH=C(CH_3)COOcC_3H_5$ | |
| 164 | H | Cl | O | $CF_3$ | $CH_3$ | H | H | $CH=C(CH_3)COOcC_4H_7$ | |
| 165 | H | Cl | O | $CF_3$ | $CH_3$ | H | H | $CH=C(CH_3)COOcC_5H_9$ | |
| 166 | H | Cl | O | $CF_3$ | $CH_3$ | H | H | $CH=CHCOCH_3$ | |
| 167 | H | Cl | O | $CF_3$ | $CH_3$ | H | H | $CH=CHCOC_2H_5$ | |
| 168 | H | Cl | O | $CF_3$ | $CH_3$ | H | H | $CH=C(CH_3)COCH_3$ | |
| 169 | H | Cl | O | $CF_3$ | $CH_3$ | H | H | $CH=CHCOCH_2Cl$ | |
| 170 | H | Cl | O | $CF_3$ | $CH_3$ | H | H | $CH=CHCOCH_2CH_2OCH_3$ | |
| 171 | H | Cl | O | $CF_3$ | $CH_3$ | H | H | $CH=CHCOcC_3H_5$ | |
| 172 | H | Cl | O | $CF_3$ | $CH_3$ | H | H | $CH=CHCOcC_4H_7$ | |
| 173 | H | Cl | O | $CF_3$ | $CH_3$ | H | H | $CH=CHCOcC_5H_9$ | |
| 174 | H | Cl | O | $CF_3$ | $CH_3$ | H | H | $CH=CHCOcC_6H_{11}$ | |
| 175 | H | Cl | O | $CF_3$ | $CH_3$ | H | H | $CH=C(CH_3)COcC_5H_9$ | |
| 176 | H | Cl | O | $CF_3$ | $CH_3$ | H | H | $CH=C(CH_3)COcC_6H_{11}$ | |
| 177 | H | Cl | O | $CF_3$ | $CH_3$ | H | $CH_3$ | $CH=CHCOOCH_3$ | |
| 178 | H | Cl | O | $CF_3$ | $CH_3$ | H | $CH_3$ | $CH=CHCOOC_2H_5$ | |
| 179 | F | Cl | O | $CF_3$ | H | H | H | $cC_3H_5$ | |
| 180 | F | Cl | O | $CF_3$ | H | H | H | $cC_4H_7$ | |
| 181 | F | Cl | O | $CF_3$ | H | H | H | $cC_5H_9$ | |
| 182 | F | Cl | O | $CF_3$ | H | H | H | $cC_6H_{11}$ | |
| 183 | F | Cl | O | $CF_3$ | H | H | H | CHO | |
| 184 | F | Cl | O | $CF_3$ | H | H | H | $CH_2C_6H_5$ | |
| 185 | F | Cl | O | $CF_3$ | H | H | H | $CH(O)CH_2$ | |
| 186 | F | Cl | O | $CF_3$ | H | H | H | $CH(O)CHCH_3$ | |
| 187 | F | Cl | O | $CF_3$ | H | H | H | $CH_2CH(O)CH_2$ | |
| 188 | F | Cl | O | $CF_3$ | H | H | H | $CH_2CH_2CH(O)CH_2$ | |
| 189 | F | Cl | O | $CF_3$ | H | H | H | $CH_2cC_3H_5$ | |
| 190 | F | Cl | O | $CF_3$ | H | H | H | $(CH_2)_2cC_3H_5$ | |
| 191 | F | Cl | O | $CF_3$ | H | H | H | $CH_2cC_4H_7$ | |
| 192 | F | Cl | O | $CF_3$ | H | H | H | $CH_2cC_6H_{11}$ | |
| 193 | F | Cl | O | $CF_3$ | H | H | H | $CH_2CHO$ | |
| 194 | F | Cl | O | $CF_3$ | H | H | H | $(CH_2)_2CHO$ | |
| 195 | F | Cl | O | $CF_3$ | H | H | H | $(CH_2)_3CHO$ | |
| 196 | F | Cl | O | $CF_3$ | H | H | H | $CH(CH_3)CHO$ | |
| 197 | F | Cl | O | $CF_3$ | H | H | H | $CH=CHcC_3H_5$ | |
| 198 | F | Cl | O | $CF_3$ | H | H | H | $CH=CHCH_2cC_3H_5$ | |
| 199 | F | Cl | O | $CF_3$ | H | H | H | $CH=CHCH_2cC_4H_7$ | |
| 200 | F | Cl | O | $CF_3$ | H | H | H | $CH=CHCHO$ | |
| 201 | F | Cl | O | $CF_3$ | H | H | H | $CH=C(CH_3)CHO$ | |
| 202 | F | Cl | O | $CF_3$ | H | H | H | $CH(OR^6)_2$ | $CH_3$ |
| 203 | F | Cl | O | $CF_3$ | H | H | H | $CH(OR^6)_2$ | $C_2H_5$ |
| 204 | F | Cl | O | $CF_3$ | H | H | H | $CH(OR^6)_2$ | $nC_3H_7$ |
| 205 | F | Cl | O | $CF_3$ | H | H | H | $CH(OR^6)(OR^7)$ | $(CH_2)_2$ |
| 206 | F | Cl | O | $CF_3$ | H | H | H | $CH(OR^6)(OR^7)$ | $(CH_2)_3$ |
| 207 | F | Cl | O | $CF_3$ | H | H | H | $CH(OR^6)(OR^7)$ | $(CH_2)_4$ |
| 208 | F | Cl | O | $CF_3$ | H | H | H | $CH_2CH(OR^6)_2$ | $CH_3$ |
| 209 | F | Cl | O | $CF_3$ | H | H | H | $CH_2CH(OR^6)_2$ | $C_2H_5$ |
| 210 | F | Cl | O | $CF_3$ | H | H | H | $CH_2CH(OR^6)(OR^7)$ | $(CH_2)_2$ |
| 211 | F | Cl | O | $CF_3$ | H | H | H | $CH_2CH(OR^6)(OR^7)$ | $(CH_2)_3$ |
| 212 | F | Cl | O | $CF_3$ | H | H | H | $CH_2CH_2CH(OR^6)_2$ | $CH_3$ |
| 213 | F | Cl | O | $CF_3$ | H | H | H | $CH_2CH_2CH(OR^6)_2$ | $C_2H_5$ |
| 214 | F | Cl | O | $CF_3$ | H | H | H | $CH_2CH_2CH(OR^6)(OR^7)$ | $(CH_2)_2$ |
| 215 | F | Cl | O | $CF_3$ | H | H | H | $CH_2CH_2CH(OR^6)(OR^7)$ | $(CH_2)_3$ |
| 216 | F | Cl | O | $CF_3$ | H | H | H | $CH=CHCH(OR^6)_2$ | $CH_3$ |
| 217 | F | Cl | O | $CF_3$ | H | H | H | $CH=CHCH(OR^6)_2$ | $C_2H_5$ |
| 218 | F | Cl | O | $CF_3$ | H | H | H | $CH(CH_3)CH(OR^6)_2$ | $CH_3$ |
| 219 | F | Cl | O | $CF_3$ | H | H | H | $CH(CH_3)CH(OR^6)(OR^7)$ | $(CH_2)_2$ |
| 220 | F | Cl | O | $CF_3$ | H | H | H | $CH(SR^6)_2$ | $CH_3$ |
| 221 | F | Cl | O | $CF_3$ | H | H | H | $CH(SR^6)_2$ | $C_2H_5$ |
| 222 | F | Cl | O | $CF_3$ | H | H | H | $CH(SR^6)_2$ | $nC_3H_7$ |
| 223 | F | Cl | O | $CF_3$ | H | H | H | $CH(SR^6)(SR^7)$ | $(CH_2)_2$ |
| 224 | F | Cl | O | $CF_3$ | H | H | H | $CH(SR^6)(SR^7)$ | $(CH_2)_3$ |
| 225 | F | Cl | O | $CF_3$ | H | H | H | $CH(SR^6)(SR^7)$ | $(CH_2)_4$ |
| 226 | F | Cl | O | $CF_3$ | H | H | H | $CH_2CH(SR^6)_2$ | $CH_3$ |
| 227 | F | Cl | O | $CF_3$ | H | H | H | $CH_2CH(SR^6)_2$ | $C_2H_5$ |
| 228 | F | Cl | O | $CF_3$ | H | H | H | $CH_2CH(SR^6)(SR^7)$ | $(CH_2)_2$ |
| 229 | F | Cl | O | $CF_3$ | H | H | H | $CH_2CH(SR^6)(SR^7)$ | $(CH_2)_3$ |
| 230 | F | Cl | O | $CF_3$ | H | H | H | $CH_2CH_2CH(SR^6)_2$ | $CH_3$ |
| 231 | F | Cl | O | $CF_3$ | H | H | H | $CH_2CH_2CH(SR^6)_2$ | $C_2H_5$ |
| 232 | F | Cl | O | $CF_3$ | H | H | H | $CH_2CH_2CH(SR^6)(SR^7)$ | $(CH_2)_2$ |
| 233 | F | Cl | O | $CF_3$ | H | H | H | $CH_2CH_2CH(SR^6)(SR^7)$ | $(CH_2)_3$ |
| 234 | F | Cl | O | $CF_3$ | H | H | H | $CH=CHCH(SR^6)_2$ | $CH_3$ |
| 235 | F | Cl | O | $CF_3$ | H | H | H | $CH=CHCH(SR^6)_3$ | $C_2H_5$ |

TABLE 1-continued

| Compound No. | X | Y | Z¹ | R¹ | R² | R³ | R⁴ | R⁵ | R⁶ or R⁶–R⁷ |
|---|---|---|---|---|---|---|---|---|---|
| 236 | F | Cl | O | $CF_3$ | H | H | H | CH=CHCOOH | |
| 237 | F | Cl | O | $CF_3$ | H | H | H | CH=C($CH_3$)COOH | |
| 238 | F | Cl | O | $CF_3$ | H | H | H | CH=CHCOO$CH_3$ | |
| 239 | F | Cl | O | $CF_3$ | H | H | H | CH=CHCOO$C_2H_5$ | |
| 240 | F | Cl | O | $CF_3$ | H | H | H | CH=CHCOOn$C_3H_7$ | |
| 241 | F | Cl | O | $CF_3$ | H | H | H | CH=CHCOOi$C_3H_7$ | |
| 242 | F | Cl | O | $CF_3$ | H | H | H | CH=C($CH_3$)COO$CH_3$ | |
| 243 | F | Cl | O | $CF_3$ | H | H | H | CH=C($CH_3$)COO$C_2H_5$ | |
| 244 | F | Cl | O | $CF_3$ | H | H | H | CH=C($CH_3$)COOn$C_3H_7$ | |
| 245 | F | Cl | O | $CF_3$ | H | H | H | CH=C($CH_3$)COOi$C_3H_7$ | |
| 246 | F | Cl | O | $CF_3$ | H | H | H | CH=CHCOO$CH_2CH_2$Cl | |
| 247 | F | Cl | O | $CF_3$ | H | H | H | CH=CHCOO$CH_2$O$CH_3$ | |
| 248 | F | Cl | O | $CF_3$ | H | H | H | CH=C($CH_3$)COO$CH_2$O$CH_3$ | |
| 249 | F | Cl | O | $CF_3$ | H | H | H | CH=CHCOOc$C_3H_5$ | |
| 250 | F | Cl | O | $CF_3$ | H | H | H | CH=CHCOOc$C_4H_7$ | |
| 251 | F | Cl | O | $CF_3$ | H | H | H | CH=CHCOOc$C_5H_9$ | |
| 252 | F | Cl | O | $CF_3$ | H | H | H | CH=C($CH_3$)COOc$C_3H_5$ | |
| 253 | F | Cl | O | $CF_3$ | H | H | H | CH=C($CH_3$)COOc$C_4H_7$ | |
| 254 | F | Cl | O | $CF_3$ | H | H | H | CH=C($CH_3$)COOc$C_5H_9$ | |
| 255 | F | Cl | O | $CF_3$ | H | H | H | CH=CHCO$CH_3$ | |
| 256 | F | Cl | O | $CF_3$ | H | H | H | CH=CHCO$C_2H_5$ | |
| 257 | F | Cl | O | $CF_3$ | H | H | H | CH=C($CH_3$)CO$CH_3$ | |
| 258 | F | Cl | O | $CF_3$ | H | H | H | CH=CHCO$CH_2$Cl | |
| 259 | F | Cl | O | $CF_3$ | H | H | H | CH=CHCO$CH_2CH_2$O$CH_3$ | |
| 260 | F | Cl | O | $CF_3$ | H | H | H | CH=CHCOc$C_3H_5$ | |
| 261 | F | Cl | O | $CF_3$ | H | H | H | CH=CHCOc$C_4H_7$ | |
| 262 | F | Cl | O | $CF_3$ | H | H | H | CH=CHCOc$C_5H_9$ | |
| 263 | F | Cl | O | $CF_3$ | H | H | H | CH=CHCOc$C_6H_{11}$ | |
| 264 | F | Cl | O | $CF_3$ | H | H | H | CH=C($CH_3$)COc$C_5H_9$ | |
| 265 | F | Cl | O | $CF_3$ | H | H | H | CH=C($CH_3$)COc$C_6H_{11}$ | |
| 266 | F | Cl | O | $CF_3$ | H | H | $CH_3$ | CH=CHCOO$CH_3$ | |
| 267 | F | Cl | O | $CF_3$ | H | H | $CH_3$ | CH=CHCOO$C_2H_5$ | |
| 268 | F | Cl | O | $CF_3$ | $CH_3$ | H | H | c$C_3H_5$ | |
| 269 | F | Cl | O | $CF_3$ | $CH_3$ | H | H | c$C_4H_7$ | |
| 270 | F | Cl | O | $CF_3$ | $CH_3$ | H | H | c$C_5H_9$ | |
| 271 | F | Cl | O | $CF_3$ | $CH_3$ | H | H | c$C_6H_{11}$ | |
| 272 | F | Cl | O | $CF_3$ | $CH_3$ | H | H | CHO | |
| 273 | F | Cl | O | $CF_3$ | $CH_3$ | H | H | $CH_2C_6H_5$ | |
| 274 | F | Cl | O | $CF_3$ | $CH_3$ | H | H | CH(O)$CH_2$ | |
| 275 | F | Cl | O | $CF_3$ | $CH_3$ | H | H | CH(O)CH$CH_3$ | |
| 276 | F | Cl | O | $CF_3$ | $CH_3$ | H | H | $CH_2$CH(O)$CH_2$ | |
| 277 | F | Cl | O | $CF_3$ | $CH_3$ | H | H | $CH_2CH_2$CH(O)$CH_2$ | |
| 278 | F | Cl | O | $CF_3$ | $CH_3$ | H | H | $CH_2$c$C_3$H | |
| 279 | F | Cl | O | $CF_3$ | $CH_3$ | H | H | ($CH_2$)$_2$c$C_3$H | |
| 280 | F | Cl | O | $CF_3$ | $CH_3$ | H | H | $CH_2$c$C_4H_7$ | |
| 281 | F | Cl | O | $CF_3$ | $CH_3$ | H | H | $CH_2$c$C_6H_{11}$ | |
| 282 | F | Cl | O | $CF_3$ | $CH_3$ | H | H | $CH_2$CHO | |
| 283 | F | Cl | O | $CF_3$ | $CH_3$ | H | H | ($CH_2$)$_2$CHO | |
| 284 | F | Cl | O | $CF_3$ | $CH_3$ | H | H | ($CH_2$)$_3$CHO | |
| 285 | F | Cl | O | $CF_3$ | $CH_3$ | H | H | CH($CH_3$)CHO | |
| 286 | F | Cl | O | $CF_3$ | $CH_3$ | H | H | CH=CHc$C_3H_5$ | |
| 287 | F | Cl | O | $CF_3$ | $CH_3$ | H | H | CH=CH$CH_2$c$C_3H_5$ | |
| 288 | F | Cl | O | $CF_3$ | $CH_3$ | H | H | CH=CH$CH_2$c$C_4H_7$ | |
| 289 | F | Cl | O | $CF_3$ | $CH_3$ | H | H | CH=CHCHO | |
| 290 | F | Cl | O | $CF_3$ | $CH_3$ | H | H | CH=C($CH_3$)CHO | |
| 291 | F | Cl | O | $CF_3$ | $CH_3$ | H | H | CH(OR⁶)$_2$ | $CH_3$ |
| 292 | F | Cl | O | $CF_3$ | $CH_3$ | H | H | CH(OR⁶)$_2$ | $C_2H_5$ |
| 293 | F | Cl | O | $CF_3$ | $CH_3$ | H | H | CH(OR⁶)$_2$ | n$C_3H_7$ |
| 294 | F | Cl | O | $CF_3$ | $CH_3$ | H | H | CH(OR⁶)(OR⁷) | ($CH_2$)$_2$ |
| 295 | F | Cl | O | $CF_3$ | $CH_3$ | H | H | CH(OR⁶)(OR⁷) | ($CH_2$)$_3$ |
| 296 | F | Cl | O | $CF_3$ | $CH_3$ | H | H | CH(OR⁶)(OR⁷) | ($CH_2$)$_4$ |
| 297 | F | Cl | O | $CF_3$ | $CH_3$ | H | H | $CH_2$CH(OR⁶)$_2$ | $CH_3$ |
| 298 | F | Cl | O | $CF_3$ | $CH_3$ | H | H | $CH_2$CH(OR⁶)$_2$ | $C_2H_5$ |
| 299 | F | Cl | O | $CF_3$ | $CH_3$ | H | H | $CH_2$CH(OR⁶)(OR⁷) | ($CH_2$)$_2$ |
| 300 | F | Cl | O | $CF_3$ | $CH_3$ | H | H | $CH_2$CH(OR⁶)(OR⁷) | ($CH_2$)$_3$ |
| 301 | F | Cl | O | $CF_3$ | $CH_3$ | H | H | $CH_2CH_2$CH(OR⁶)$_2$ | $CH_3$ |
| 302 | F | Cl | O | $CF_3$ | $CH_3$ | H | H | $CH_2CH_2$CH(OR⁶)$_2$ | $C_2H_5$ |
| 303 | F | Cl | O | $CF_3$ | $CH_3$ | H | H | $CH_2CH_2$CH(OR⁶)(OR⁷) | ($CH_2$)$_2$ |
| 304 | F | Cl | O | $CF_3$ | $CH_3$ | H | H | $CH_2CH_2$CH(OR⁶)(OR⁷) | ($CH_2$)$_3$ |
| 305 | F | Cl | O | $CF_3$ | $CH_3$ | H | H | CH=CHCH(OR⁶)$_2$ | $CH_3$ |
| 306 | F | Cl | O | $CF_3$ | $CH_3$ | H | H | CH=CHCH(OR⁶)$_2$ | $C_2H_5$ |
| 307 | F | Cl | O | $CF_3$ | $CH_3$ | H | H | CH($CH_3$)CH(OR⁶)$_2$ | $CH_3$ |
| 308 | F | Cl | O | $CF_3$ | $CH_3$ | H | H | CH($CH_3$)CH(OR⁶)(OR⁷) | ($CH_2$)$_2$ |
| 309 | F | Cl | O | $CF_3$ | $CH_3$ | H | H | CH(SR⁶)$_2$ | $CH_3$ |
| 310 | F | Cl | O | $CF_3$ | $CH_3$ | H | H | CH(SR⁶)$_2$ | $C_2H_5$ |
| 311 | F | Cl | O | $CF_3$ | $CH_3$ | H | H | CH(SR⁶)$_2$ | n$C_3H_7$ |

TABLE 1-continued

| Compound No. | X | Y | $Z^1$ | $R^1$ | $R^2$ | $R^3$ | $R^4$ | $R^5$ | $R^6$ or $R^6$–$R^7$ |
|---|---|---|---|---|---|---|---|---|---|
| 312 | F | Cl | O | $CF_3$ | $CH_3$ | H | H | $CH(SR^6)(SR^7)$ | $(CH_2)_2$ |
| 313 | F | Cl | O | $CF_3$ | $CH_3$ | H | H | $CH(SR^6)(SR^7)$ | $(CH_2)_3$ |
| 314 | F | Cl | O | $CF_3$ | $CH_3$ | H | H | $CH(SR^6)(SR^7)$ | $(CH_2)_4$ |
| 315 | F | Cl | O | $CF_3$ | $CH_3$ | H | H | $CH_2CH(SR^6)_2$ | $CH_3$ |
| 316 | F | Cl | O | $CF_3$ | $CH_3$ | H | H | $CH_2CH(SR^6)_2$ | $C_2H_5$ |
| 317 | F | Cl | O | $CF_3$ | $CH_3$ | H | H | $CH_2CH(SR^6)(SR^7)$ | $(CH_2)_2$ |
| 318 | F | Cl | O | $CF_3$ | $CH_3$ | H | H | $CH_2CH(SR^6)(SR^7)$ | $(CH_2)_3$ |
| 319 | F | Cl | O | $CF_3$ | $CH_3$ | H | H | $CH_2CH_2CH(SR^6)_2$ | $CH_3$ |
| 320 | F | Cl | O | $CF_3$ | $CH_3$ | H | H | $CH_2CH_2CH(SR^6)_2$ | $C_2H_5$ |
| 321 | F | Cl | O | $CF_3$ | $CH_3$ | H | H | $CH_2CH_2CH(SR^6)(SR^7)$ | $(CH_2)_2$ |
| 322 | F | Cl | O | $CF_3$ | $CH_3$ | H | H | $CH_2CH_2CH(SR^6)(SR^7)$ | $(CH_2)_3$ |
| 323 | F | Cl | O | $CF_3$ | $CH_3$ | H | H | $CH=CHCH(SR^6)_2$ | $CH_3$ |
| 324 | F | Cl | O | $CF_3$ | $CH_3$ | H | H | $CH=CHCH(SR^6)_3$ | $C_2H_5$ |
| 325 | F | Cl | O | $CF_3$ | $CH_3$ | H | H | $CH=CHCOOH$ | |
| 326 | F | Cl | O | $CF_3$ | $CH_3$ | H | H | $CH=C(CH_3)COOH$ | |
| 327 | F | Cl | O | $CF_3$ | $CH_3$ | H | H | $CH=CHCOOCH_3$ | |
| 328 | F | Cl | O | $CF_3$ | $CH_3$ | H | H | $CH=CHCOOC_2H_5$ | |
| 329 | F | Cl | O | $CF_3$ | $CH_3$ | H | H | $CH=CHCOOnC_3H_7$ | |
| 330 | F | Cl | O | $CF_3$ | $CH_3$ | H | H | $CH=CHCOOiC_3H_7$ | |
| 331 | F | Cl | O | $CF_3$ | $CH_3$ | H | H | $CH=C(CH_3)COOCH_3$ | |
| 332 | F | Cl | O | $CF_3$ | $CH_3$ | H | H | $CH=C(CH_3)COOC_2H_5$ | |
| 333 | F | Cl | O | $CF_3$ | $CH_3$ | H | H | $CH=C(CH_3)COOnC_3H_7$ | |
| 334 | F | Cl | O | $CF_3$ | $CH_3$ | H | H | $CH=C(CH_3)COOiC_3H_7$ | |
| 335 | F | Cl | O | $CF_3$ | $CH_3$ | H | H | $CH=CHCOOCH_2CH_2Cl$ | |
| 336 | F | Cl | O | $CF_3$ | $CH_3$ | H | H | $CH=CHCOOCH_2OCH_3$ | |
| 337 | F | Cl | O | $CF_3$ | $CH_3$ | H | H | $CH=C(CH_3)COOCH_2OCH_3$ | |
| 338 | F | Cl | O | $CF_3$ | $CH_3$ | H | H | $CH=CHCOOcC_3H_5$ | |
| 339 | F | Cl | O | $CF_3$ | $CH_3$ | H | H | $CH=CHCOOcC_4H_7$ | |
| 340 | F | Cl | O | $CF_3$ | $CH_3$ | H | H | $CH=CHCOOcC_5H_9$ | |
| 341 | F | Cl | O | $CF_3$ | $CH_3$ | H | H | $CH=C(CH_3)COOcC_3H_5$ | |
| 342 | F | Cl | O | $CF_3$ | $CH_3$ | H | H | $CH=C(CH_3)COOcC_4H_7$ | |
| 343 | F | Cl | O | $CF_3$ | $CH_3$ | H | H | $CH=C(CH_3)COOcC_5H_9$ | |
| 344 | F | Cl | O | $CF_3$ | $CH_3$ | H | H | $CH=CHCOCH_3$ | |
| 345 | F | Cl | O | $CF_3$ | $CH_3$ | H | H | $CH=CHCOC_2H_5$ | |
| 346 | F | Cl | O | $CF_3$ | $CH_3$ | H | H | $CH=C(CH_3)COCH_3$ | |
| 347 | F | Cl | O | $CF_3$ | $CH_3$ | H | H | $CH=CHCOCH_2Cl$ | |
| 348 | F | Cl | O | $CF_3$ | $CH_3$ | H | H | $CH=CHCOCH_2CH_2OCH_3$ | |
| 349 | F | Cl | O | $CF_3$ | $CH_3$ | H | H | $CH=CHCOcC_3H_5$ | |
| 350 | F | Cl | O | $CF_3$ | $CH_3$ | H | H | $CH=CHCOcC_4H_7$ | |
| 351 | F | Cl | O | $CF_3$ | $CH_3$ | H | H | $CH=CHCOcC_5H_9$ | |
| 352 | F | Cl | O | $CF_3$ | $CH_3$ | H | H | $CH=CHCOcC_6H_{11}$ | |
| 353 | F | Cl | O | $CF_3$ | $CH_3$ | H | H | $CH=C(CH_3)COcC_5H_9$ | |
| 354 | F | Cl | O | $CF_3$ | $CH_3$ | H | H | $CH=C(CH_3)COcC_6H_{11}$ | |
| 355 | F | Cl | O | $CF_3$ | $CH_3$ | H | $CH_3$ | $CH=CHCOOCH_3$ | |
| 356 | F | Cl | O | $CF_3$ | $CH_3$ | H | $CH_3$ | $CH=CHCOOC_2H_5$ | |
| 357 | Cl | Cl | O | $CF_3$ | H | H | H | $cC_3H_5$ | |
| 358 | Cl | Cl | O | $CF_3$ | H | H | H | $cC_4H_7$ | |
| 359 | Cl | Cl | O | $CF_3$ | H | H | H | $cC_5H_9$ | |
| 360 | Cl | Cl | O | $CF_3$ | H | H | H | $cC_6H_{11}$ | |
| 361 | Cl | Cl | O | $CF_3$ | H | H | H | CHO | |
| 362 | Cl | Cl | O | $CF_3$ | H | H | H | $CH_2C_6H_5$ | |
| 363 | Cl | Cl | O | $CF_3$ | H | H | H | $CH(O)CH_2$ | |
| 364 | Cl | Cl | O | $CF_3$ | H | H | H | $CH(O)CHCH_3$ | |
| 365 | Cl | Cl | O | $CF_3$ | H | H | H | $CH_2CH(O)CH_2$ | |
| 366 | Cl | Cl | O | $CF_3$ | H | H | H | $CH_2CH_2CH(O)CH_2$ | |
| 367 | Cl | Cl | O | $CF_3$ | H | H | H | $CH_2cC_3H_5$ | |
| 368 | Cl | Cl | O | $CF_3$ | H | H | H | $(CH_2)_2cC_3H_5$ | |
| 369 | Cl | Cl | O | $CF_3$ | H | H | H | $CH_2cC_4H_7$ | |
| 370 | Cl | Cl | O | $CF_3$ | H | H | H | $CH_2cC_6H_{11}$ | |
| 371 | Cl | Cl | O | $CF_3$ | H | H | H | $CH_2CHO$ | |
| 372 | Cl | Cl | O | $CF_3$ | H | H | H | $(CH_2)_2CHO$ | |
| 373 | Cl | Cl | O | $CF_3$ | H | H | H | $(CH_2)_3CHO$ | |
| 374 | Cl | Cl | O | $CF_3$ | H | H | H | $CH(CH_3)CHO$ | |
| 375 | Cl | Cl | O | $CF_3$ | H | H | H | $CH=CHcC_3H_5$ | |
| 376 | Cl | Cl | O | $CF_3$ | H | H | H | $CH=CHCH_2cC_3H_5$ | |
| 377 | Cl | Cl | O | $CF_3$ | H | H | H | $CH=CHCH_2cC_4H_7$ | |
| 378 | Cl | Cl | O | $CF_3$ | H | H | H | $CH=CHCHO$ | |
| 379 | Cl | Cl | O | $CF_3$ | H | H | H | $CH=C(CH_3)CHO$ | |
| 380 | Cl | Cl | O | $CF_3$ | H | H | H | $CH(OR^6)_2$ | $CH_3$ |
| 381 | Cl | Cl | O | $CF_3$ | H | H | H | $CH(OR^6)_2$ | $C_2H_5$ |
| 382 | Cl | Cl | O | $CF_3$ | H | H | H | $CH(OR^6)_2$ | $nC_3H_7$ |
| 383 | Cl | Cl | O | $CF_3$ | H | H | H | $CH(OR^6)(OR^7)$ | $(CH_2)_2$ |
| 384 | Cl | Cl | O | $CF_3$ | H | H | H | $CH(OR^6)(OR^7)$ | $(CH_2)_3$ |
| 385 | Cl | Cl | O | $CF_3$ | H | H | H | $CH(OR^6)(OR^7)$ | $(CH_2)_4$ |
| 386 | Cl | Cl | O | $CF_3$ | H | H | H | $CH_2CH(OR^6)_2$ | $CH_3$ |
| 387 | Cl | Cl | O | $CF_3$ | H | H | H | $CH_2CH(OR^6)_2$ | $C_2H_5$ |

TABLE 1-continued

| Compound No. | X | Y | Z$^1$ | R$^1$ | R$^2$ | R$^3$ | R$^4$ | R$^5$ | R$^6$ or R$^6$–R$^7$ |
|---|---|---|---|---|---|---|---|---|---|
| 388 | Cl | Cl | O | CF$_3$ | H | H | H | CH$_2$CH(OR$^6$)(OR$^7$) | (CH$_2$)$_2$ |
| 389 | Cl | Cl | O | CF$_3$ | H | H | H | CH$_2$CH(OR$^6$)(OR$^7$) | (CH$_2$)$_3$ |
| 390 | Cl | Cl | O | CF$_3$ | H | H | H | CH$_2$CH$_2$CH(OR$^6$)$_2$ | CH$_3$ |
| 391 | Cl | Cl | O | CF$_3$ | H | H | H | CH$_2$CH$_2$CH(OR$^6$)$_2$ | C$_2$H$_5$ |
| 392 | Cl | Cl | O | CF$_3$ | H | H | H | CH$_2$CH$_2$CH(OR$^6$)(OR$^7$) | (CH$_2$)$_2$ |
| 393 | Cl | Cl | O | CF$_3$ | H | H | H | CH$_2$CH$_2$CH(OR$^6$)(OR$^7$) | (CH$_2$)$_3$ |
| 394 | Cl | Cl | O | CF$_3$ | H | H | H | CH=CHCH(OR$^6$)$_2$ | CH$_3$ |
| 395 | Cl | Cl | O | CF$_3$ | H | H | H | CH=CHCH(OR$^6$)$_2$ | C$_2$H$_5$ |
| 396 | Cl | Cl | O | CF$_3$ | H | H | H | CH(CH$_3$)CH(OR$^6$)$_2$ | CH$_3$ |
| 397 | Cl | Cl | O | CF$_3$ | H | H | H | CH(CH$_3$)CH(OR$^6$)(OR$^7$) | (CH$_2$)$_2$ |
| 398 | Cl | Cl | O | CF$_3$ | H | H | H | CH(SR$^6$)$_2$ | CH$_3$ |
| 399 | Cl | Cl | O | CF$_3$ | H | H | H | CH(SR$^6$)$_2$ | C$_2$H$_5$ |
| 400 | Cl | Cl | O | CF$_3$ | H | H | H | CH(SR$^6$)$_2$ | nC$_3$H$_7$ |
| 401 | Cl | Cl | O | CF$_3$ | H | H | H | CH(SR$^6$)(SR$^7$) | (CH$_2$)$_2$ |
| 402 | Cl | Cl | O | CF$_3$ | H | H | H | CH(SR$^6$)(SR$^7$) | (CH$_2$)$_3$ |
| 403 | Cl | Cl | O | CF$_3$ | H | H | H | CH(SR$^6$)(SR$^7$) | (CH$_2$)$_4$ |
| 404 | Cl | Cl | O | CF$_3$ | H | H | H | CH$_2$CH(SR$^6$)$_2$ | CH$_3$ |
| 405 | Cl | Cl | O | CF$_3$ | H | H | H | CH$_2$CH(SR$^6$)$_2$ | C$_2$H$_5$ |
| 406 | Cl | Cl | O | CF$_3$ | H | H | H | CH$_2$CH(SR$^6$)(SR$^7$) | (CH$_2$)$_2$ |
| 407 | Cl | Cl | O | CF$_3$ | H | H | H | CH$_2$CH(SR$^6$)(SR$^7$) | (CH$_2$)$_3$ |
| 408 | Cl | Cl | O | CF$_3$ | H | H | H | CH$_2$CH$_2$CH(SR$^6$)$_2$ | CH$_3$ |
| 409 | Cl | Cl | O | CF$_3$ | H | H | H | CH$_2$CH$_2$CH(SR$^6$)$_2$ | C$_2$H$_5$ |
| 410 | Cl | Cl | O | CF$_3$ | H | H | H | CH$_2$CH$_2$CH(SR$^6$)(SR$^7$) | (CH$_2$)$_2$ |
| 411 | Cl | Cl | O | CF$_3$ | H | H | H | CH$_2$CH$_2$CH(SR$^6$)(SR$^7$) | (CH$_2$)$_3$ |
| 412 | Cl | Cl | O | CF$_3$ | H | H | H | CH=CHCH(SR$^6$)$_2$ | CH$_3$ |
| 413 | Cl | Cl | O | CF$_3$ | H | H | H | CH=CHCH(SR$^6$)$_3$ | C$_2$H$_5$ |
| 414 | Cl | Cl | O | CF$_3$ | H | H | H | CH=CHCOOH | |
| 415 | Cl | Cl | O | CF$_3$ | H | H | H | CH=C(CH$_3$)COOH | |
| 416 | Cl | Cl | O | CF$_3$ | H | H | H | CH=CHCOOCH$_3$ | |
| 417 | Cl | Cl | O | CF$_3$ | H | H | H | CH=CHCOOC$_2$H$_5$ | |
| 418 | Cl | Cl | O | CF$_3$ | H | H | H | CH=CHCOOnC$_3$H$_7$ | |
| 419 | Cl | Cl | O | CF$_3$ | H | H | H | CH=CHCOOiC$_3$H$_7$ | |
| 420 | Cl | Cl | O | CF$_3$ | H | H | H | CH=C(CH$_3$)COOCH$_3$ | |
| 421 | Cl | Cl | O | CF$_3$ | H | H | H | CH=C(CH$_3$)COOC$_2$H$_5$ | |
| 422 | Cl | Cl | O | CF$_3$ | H | H | H | CH=C(CH$_3$)COOnC$_3$H$_7$ | |
| 423 | Cl | CT | O | CF$_3$ | H | H | H | CH=C(CH$_3$)COOiC$_3$H$_7$ | |
| 424 | Cl | Cl | O | CF$_3$ | H | H | H | CH=CHCOOCH$_2$CH$_2$Cl | |
| 425 | Cl | Cl | O | CF$_3$ | H | H | H | CH=CHCOOCH$_2$OCH$_3$ | |
| 426 | Cl | Cl | O | CF$_3$ | H | H | H | CH=C(CH$_3$)COOCH$_2$OCH$_3$ | |
| 427 | Cl | Cl | O | CF$_3$ | H | H | H | CH=CHCOOcC$_3$H$_5$ | |
| 428 | Cl | Cl | O | CF$_3$ | H | H | H | CH=CHCOOcC$_4$H$_7$ | |
| 429 | Cl | Cl | O | CF$_3$ | H | H | H | CH=CHCOOcC$_5$H$_9$ | |
| 430 | Cl | Cl | O | CF$_3$ | H | H | H | CH=C(CH$_3$)COOcC$_3$H$_5$ | |
| 431 | Cl | Cl | O | CF$_3$ | H | H | H | CH=C(CH$_3$)COOcC$_4$H$_7$ | |
| 432 | Cl | Cl | O | CF$_3$ | H | H | H | CH=C(CH$_3$)COOcC$_5$H$_9$ | |
| 433 | Cl | Cl | O | CF$_3$ | H | H | H | CH=CHCOCH$_3$ | |
| 434 | Cl | Cl | O | CF$_3$ | H | H | H | CH=CHCOC$_2$H$_5$ | |
| 435 | Cl | Cl | O | CF$_3$ | H | H | H | CH=C(CH$_3$)COCH$_3$ | |
| 436 | Cl | Cl | O | CF$_3$ | H | H | H | CH=CHCOCH$_2$Cl | |
| 437 | Cl | Cl | O | CF$_3$ | H | H | H | CH=CHCOCH$_2$CH$_2$OCH$_3$ | |
| 438 | Cl | Cl | O | CF$_3$ | H | H | H | CH=CHCOcC$_3$H$_5$ | |
| 439 | Cl | Cl | O | CF$_3$ | H | H | H | CH=CHCOcC$_4$H$_7$ | |
| 440 | Cl | Cl | O | CF$_3$ | H | H | H | CH=CHCOcC$_5$H$_9$ | |
| 441 | Cl | Cl | O | CF$_3$ | H | H | H | CH=CHCOcC$_6$H$_{11}$ | |
| 442 | Cl | Cl | O | CF$_3$ | H | H | H | CH=C(CH$_3$)COcC$_5$H$_9$ | |
| 443 | Cl | Cl | O | CF$_3$ | H | H | H | CH=C(CH$_3$)COcC$_6$H$_{11}$ | |
| 444 | Cl | Cl | O | CF$_3$ | H | H | CH$_3$ | CH=CHCOOCH$_3$ | |
| 445 | Cl | Cl | O | CF$_3$ | H | H | CH$_3$ | CH=CHCOOC$_2$H$_5$ | |
| 446 | Cl | Cl | O | CF$_3$ | CH$_3$ | H | H | cC$_3$H$_5$ | |
| 447 | Cl | Cl | O | CF$_3$ | CH$_3$ | H | H | cC$_4$H$_7$ | |
| 448 | Cl | Cl | O | CF$_3$ | CH$_3$ | H | H | cC$_5$H$_9$ | |
| 449 | Cl | Cl | O | CF$_3$ | CH$_3$ | H | H | cC$_6$H$_{11}$ | |
| 450 | Cl | Cl | O | CF$_3$ | CH$_3$ | H | H | CHO | |
| 451 | Cl | Cl | O | CF$_3$ | CH$_3$ | H | H | CH$_2$C$_6$H$_5$ | |
| 452 | Cl | Cl | O | CF$_3$ | CH$_3$ | H | H | CH(O)CH$_2$ | |
| 453 | Cl | Cl | O | CF$_3$ | CH$_3$ | H | H | CH(O)CHCH$_3$ | |
| 454 | Cl | Cl | O | CF$_3$ | CH$_3$ | H | H | CH$_2$CH(O)CH$_2$ | |
| 455 | Cl | Cl | O | CF$_3$ | CH$_3$ | H | H | CH$_2$CH$_2$CH(O)CH$_2$ | |
| 456 | Cl | Cl | O | CF$_3$ | CH$_3$ | H | H | CH$_2$cC$_3$H$_5$ | |
| 457 | Cl | Cl | O | CF$_3$ | CH$_3$ | H | H | (CH$_2$)$_2$cC$_3$H$_5$ | |
| 458 | Cl | Cl | O | CF$_3$ | CH$_3$ | H | H | CH$_2$cC$_4$H$_7$ | |
| 459 | Cl | Cl | O | CF$_3$ | CH$_3$ | H | H | CH$_2$cC$_6$H$_{11}$ | |
| 460 | Cl | Cl | O | CF$_3$ | CH$_3$ | H | H | CH$_2$CHO | |
| 461 | Cl | Cl | O | CF$_3$ | CH$_3$ | H | H | (CH$_2$)$_2$CHO | |
| 462 | Cl | Cl | O | CF$_3$ | CH$_3$ | H | H | (CH$_2$)$_3$CHO | |
| 463 | Cl | Cl | O | CF$_3$ | CH$_3$ | H | H | CH(CH$_3$)CHO | |

TABLE 1-continued

| Compound No. | X | Y | Z¹ | R¹ | R² | R³ | R⁴ | R⁵ | R⁶ or R⁶–R⁷ |
|---|---|---|---|---|---|---|---|---|---|
| 464 | Cl | Cl | O | $CF_3$ | $CH_3$ | H | H | $CH=CHcC_3H_5$ | |
| 465 | Cl | Cl | O | $CF_3$ | $CH_3$ | H | H | $CH=CHCH_2cC_3H_5$ | |
| 466 | Cl | Cl | O | $CF_3$ | $CH_3$ | H | H | $CH=CHCH_2cC_4H_7$ | |
| 467 | Cl | Cl | O | $CF_3$ | $CH_3$ | H | H | $CH=CHCHO$ | |
| 468 | Cl | Cl | O | $CF_3$ | $CH_3$ | H | H | $CH=C(CH_3)CHO$ | |
| 469 | Cl | Cl | O | $CF_3$ | $CH_3$ | H | H | $CH(OR^6)_2$ | $CH_3$ |
| 470 | Cl | Cl | O | $CF_3$ | $CH_3$ | H | H | $CH(OR^6)_2$ | $C_2H_5$ |
| 471 | Cl | Cl | O | $CF_3$ | $CH_3$ | H | H | $CH(OR^6)_2$ | $nC_3H_7$ |
| 472 | Cl | Cl | O | $CF_3$ | $CH_3$ | H | H | $CH(OR^6)(OR^7)$ | $(CH_2)_2$ |
| 473 | Cl | Cl | O | $CF_3$ | $CH_3$ | H | H | $CH(OR^6)(OR^7)$ | $(CH_2)_3$ |
| 474 | Cl | Cl | O | $CF_3$ | $CH_3$ | H | H | $CH(OR^6)(OR^7)$ | $(CH_2)_4$ |
| 475 | Cl | Cl | O | $CF_3$ | $CH_3$ | H | H | $CH_2CH(OR^6)_2$ | $CH_3$ |
| 476 | Cl | Cl | O | $CF_3$ | $CH_3$ | H | H | $CH_2CH(OR^6)_2$ | $C_2H_5$ |
| 477 | Cl | Cl | O | $CF_3$ | $CH_3$ | H | H | $CH_2CH(OR^6)(OR^7)$ | $(CH_2)_2$ |
| 478 | Cl | Cl | O | $CF_3$ | $CH_3$ | H | H | $CH_2CH(OR^6)(OR^7)$ | $(CH_2)_3$ |
| 479 | Cl | Cl | O | $CF_3$ | $CH_3$ | H | H | $CH_2CH_2CH(OR^6)_2$ | $CH_3$ |
| 480 | Cl | Cl | O | $CF_3$ | $CH_3$ | H | H | $CH_2CH_2CH(OR^6)_2$ | $C_2H_5$ |
| 481 | Cl | Cl | O | $CF_3$ | $CH_3$ | H | H | $CH_2CH_2CH(OR^6)(OR^7)$ | $(CH_2)_2$ |
| 482 | Cl | Cl | O | $CF_3$ | $CH_3$ | H | H | $CH_2CH_2CH(OR^6)(OR^7)$ | $(CH_2)_3$ |
| 483 | Cl | Cl | O | $CF_3$ | $CH_3$ | H | H | $CH=CHCH(OR^6)_2$ | $CH_3$ |
| 484 | Cl | Cl | O | $CF_3$ | $CH_3$ | H | H | $CH=CHCH(OR^6)_2$ | $C_2H_5$ |
| 485 | Cl | Cl | O | $CF_3$ | $CH_3$ | H | H | $CH(CH_3)CH(OR^6)_2$ | $CH_3$ |
| 486 | Cl | Cl | O | $CF_3$ | $CH_3$ | H | H | $CH(CH_3)CH(OR^6)(OR^7)$ | $(CH_2)_2$ |
| 487 | Cl | Cl | O | $CF_3$ | $CH_3$ | H | H | $CH(SR^6)_2$ | $CH_3$ |
| 488 | Cl | Cl | O | $CF_3$ | $CH_3$ | H | H | $CH(SR^6)_2$ | $C_2H_5$ |
| 489 | Cl | Cl | O | $CF_3$ | $CH_3$ | H | H | $CH(SR^6)_2$ | $nC_3H_7$ |
| 490 | Cl | Cl | O | $CF_3$ | $CH_3$ | H | H | $CH(SR^6)(SR^7)$ | $(CH_2)_2$ |
| 491 | Cl | Cl | O | $CF_3$ | $CH_3$ | H | H | $CH(SR^6)(SR^7)$ | $(CH_2)_3$ |
| 492 | Cl | Cl | O | $CF_3$ | $CH_3$ | H | H | $CH(SR^6)(SR^7)$ | $(CH_2)_4$ |
| 493 | Cl | Cl | O | $CF_3$ | $CH_3$ | H | H | $CH_2CH(SR^6)_2$ | $CH_3$ |
| 494 | Cl | Cl | O | $CF_3$ | $CH_3$ | H | H | $CH_2CH(SR^6)_2$ | $C_2H_5$ |
| 495 | Cl | Cl | O | $CF_3$ | $CH_3$ | H | H | $CH_2CH(SR^6)(SR^7)$ | $(CH_2)_2$ |
| 496 | Cl | Cl | O | $CF_3$ | $CH_3$ | H | H | $CH_2CH(SR^6)(SR^7)$ | $(CH_2)_3$ |
| 497 | Cl | Cl | O | $CF_3$ | $CH_3$ | H | H | $CH_2CH_2CH(SR^6)_2$ | $CH_3$ |
| 498 | Cl | Cl | O | $CF_3$ | $CH_3$ | H | H | $CH_2CH_2CH(SR^6)_2$ | $C_2H_5$ |
| 499 | Cl | Cl | O | $CF_3$ | $CH_3$ | H | H | $CH_2CH_2CH(SR^6)(SR^7)$ | $(CH_2)_2$ |
| 500 | Cl | Cl | O | $CF_3$ | $CH_3$ | H | H | $CH_2CH_2CH(SR^6)(SR^7)$ | $(CH_2)_3$ |
| 501 | Cl | Cl | O | $CF_3$ | $CH_3$ | H | H | $CH=CHCH(SR^6)_2$ | $CH_3$ |
| 502 | Cl | Cl | O | $CF_3$ | $CH_3$ | H | H | $CH=CHCH(SR^6)_3$ | $C_2H_5$ |
| 503 | Cl | Cl | O | $CF_3$ | $CH_3$ | H | H | $CH=CHCOOH$ | |
| 504 | Cl | Cl | O | $CF_3$ | $CH_3$ | H | H | $CH=C(CH_3)COOH$ | |
| 505 | Cl | Cl | O | $CF_3$ | $CH_3$ | H | H | $CH=CHCOOCH_3$ | |
| 506 | Cl | Cl | O | $CF_3$ | $CH_3$ | H | H | $CH=CHCOOC_2H_5$ | |
| 507 | Cl | Cl | O | $CF_3$ | $CH_3$ | H | H | $CH=CHCOOnC_3H_7$ | |
| 508 | Cl | Cl | O | $CF_3$ | $CH_3$ | H | H | $CH=CHCOOiC_3H_7$ | |
| 509 | Cl | Cl | O | $CF_3$ | $CH_3$ | H | H | $CH=C(CH_3)COOCH_3$ | |
| 510 | Cl | Cl | O | $CF_3$ | $CH_3$ | H | H | $CH=C(CH_3)COOC_2H_5$ | |
| 511 | Cl | Cl | O | $CF_3$ | $CH_3$ | H | H | $CH=C(CH_3)COOnC_3H_7$ | |
| 512 | Cl | Cl | O | $CF_3$ | $CH_3$ | H | H | $CH=C(CH_3)COOiC_3H_7$ | |
| 513 | Cl | Cl | O | $CF_3$ | $CH_3$ | H | H | $CH=CHCOOCH_2CH_2Cl$ | |
| 514 | Cl | Cl | O | $CF_3$ | $CH_3$ | H | H | $CH=CHCOOCH_2OCH_3$ | |
| 515 | Cl | Cl | O | $CF_3$ | $CH_3$ | H | H | $CH=C(CH_3)COOCH_2OCH_3$ | |
| 516 | Cl | Cl | O | $CF_3$ | $CH_3$ | H | H | $CH=CHCOOcC_3H_5$ | |
| 517 | Cl | Cl | O | $CF_3$ | $CH_3$ | H | H | $CH=CHCOOcC_4H_7$ | |
| 518 | Cl | Cl | O | $CF_3$ | $CH_3$ | H | H | $CH=CHCOOcC_5H_9$ | |
| 519 | Cl | Cl | O | $CF_3$ | $CH_3$ | H | H | $CH=C(CH_3)COOcC_3H_5$ | |
| 520 | Cl | Cl | O | $CF_3$ | $CH_3$ | H | H | $CH=C(CH_3)COOcC_4H_7$ | |
| 521 | Cl | Cl | O | $CF_3$ | $CH_3$ | H | H | $CH=C(CH_3)COOcC_5H_9$ | |
| 522 | Cl | Cl | O | $CF_3$ | $CH_3$ | H | H | $CH=CHCOCH_3$ | |
| 523 | Cl | Cl | O | $CF_3$ | $CH_3$ | H | H | $CH=CHCOC_2H_5$ | |
| 524 | Cl | Cl | O | $CF_3$ | $CH_3$ | H | H | $CH=C(CH_3)COCH_3$ | |
| 525 | Cl | Cl | O | $CF_3$ | $CH_3$ | H | H | $CH=CHCOCH_2Cl$ | |
| 526 | Cl | Cl | O | $CF_3$ | $CH_3$ | H | H | $CH=CHCOCH_2CH_2OCH_3$ | |
| 527 | Cl | Cl | O | $CF_3$ | $CH_3$ | H | H | $CH=CHCOcC_3H_5$ | |
| 528 | Cl | Cl | O | $CF_3$ | $CH_3$ | H | H | $CH=CHCOcC_4H_7$ | |
| 529 | Cl | Cl | O | $CF_3$ | $CH_3$ | H | H | $CH=CHCOcC_5H_9$ | |
| 530 | Cl | Cl | O | $CF_3$ | $CH_3$ | H | H | $CH=CHCOcC_6H_{11}$ | |
| 531 | Cl | Cl | O | $CF_3$ | $CH_3$ | H | H | $CH=C(CH_3)COcC_5H_9$ | |
| 532 | Cl | Cl | O | $CF_3$ | $CH_3$ | H | H | $CH=C(CH_3)COcC_6H_{11}$ | |
| 533 | Cl | Cl | O | $CF_3$ | $CH_3$ | H | $CH_3$ | $CH=CHCOOCH_3$ | |
| 534 | Cl | Cl | O | $CF_3$ | $CH_3$ | H | $CH_3$ | $CH=CHCOOC_2H_5$ | |

The following will describe a reference production example for intermediate 1.

Reference Production Example

First, 32.3 g of 5-amino-2-chloro-4-fluorophenol (this compound was produced by the process disclosed in the published specification of European Patent Application, EP-61741-A) was mixed with 150 ml of concentrated hydrochloric acid, and the mixture was stirred at 50° C. for 30 minutes. To this mixture was added dropwise at 0° C. over 10 minutes a solution of 15 g of sodium nitrite dissolved in 40 ml of water. The mixture was stirred at 0° C. for 1 hour and then cooled to −50° C. To this mixture was rapidly added dropwise at −50° C. a solution of 132 g of tin (II) chloride dissolved in 132 g of concentrated hydrochloric acid, and the mixture was slowly returned to room temperature and then further stirred at room temperature for 1 hour. The resulting solids were collected by filtration, and dried at 80° C. under reduced pressure, which afforded 75 g of crude crystals of 2-fluoro-4-chloro-5-hydroxyphenylhydrazine hydrochloride.

$^1$H-NMR (DMSO-$d_6$, TMS, δ (ppm)): 3–5 (2H, br), 6.73 (1H, d), 7.22 (1H, d), 8.20 (1H, s), 9–11 (2H, br).

Then, 49.2 g of sodium acetate and 40.5 g of 1,1-dibromo-3,3,3-trifluoroacetone were dissolved in 400 ml of water, and the solution was heated at 80° to 90° C. for 40 minutes. This solution was cooled to 0° C., to which 75 g of the crude crystals of 2-fluoro-4-chloro-5-hydroxyphenylhydrazine hydrochloride was added. The mixture was stirred at room temperature for 70 minutes, and the resulting crystals were collected by filtration, and dried under reduced pressure, which afforded 35.4 g of 3,3,3-trifluoro-2-oxopropanal 1-(4-chloro-2-fluoro-5-hydroxyphenylhydrazone).

$^1$H-NMR (300 MHz, CDCl$_3$, TMS, δ (ppm)): 5.49 (1H, s), 7.15 (1H, d, J=10.5 Hz), 7.24 (1H, d, J=7.4 Hz), 7.38 (1H, q, J=1.8 Hz), 8.75 (1H, s).

Then, 12.9 g of 3,3,3-trifluoro-2-oxopropanal 1-(4-chloro-2-fluoro-5-hyroxyphenylhydrazone) thus obtained and 22.3 g of (carbethoxyethylidene) triphenylphosphorane were dissolved in 110 ml of THF, and the solution was heated under reflux for 3 hours. The solvent was evaporated under reduced pressure, and the residue was subjected to silica gel column chromatography, which afforded 8.8 g of 2-(2-fluoro-4-chloro-5-hydroxyphenyl)-4-methyl-5-tifluoromethylpyridazin-3-one (intermediate 1).

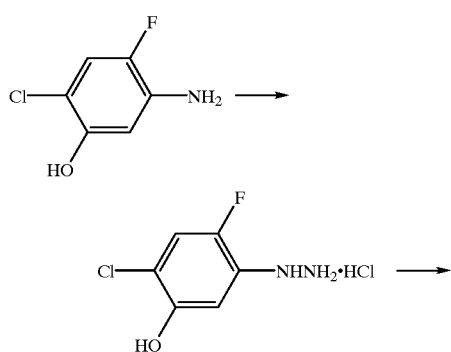

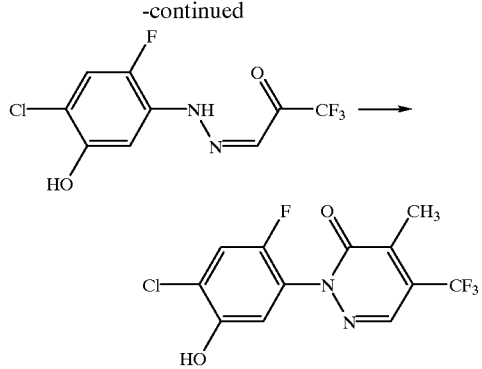

The following will describe formulation examples, in which the present compounds are designated by their compound numbers shown in Table 1, and parts are by weight.

Formulation Example 1

Fifty parts of each of the present compounds 1 to 534, 3 parts of calcium lignin sulfonate, 2 parts of sodium laurylsulfate, and 45 parts of synthetic hydrated silicon oxide are well pulverized and mixed to give a wettable powder for each compound.

Formulation Example 2

Ten parts of each of the present compounds 1 to 534, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

Formulation Example 3

Two parts of each of the present compounds 1 to 534, 2 parts of synthetic hydrated silicon oxide, 2 parts of calcium lignin sulfonate, 30 parts of bentonite, and 64 parts of kaolin clay are well pulverized and mixed. The mixture is well kneaded with the addition of water, and then granulated and dried to give a granule for each compound.

Formulation Example 4

Twenty-five parts of each of the present compounds 1 to 534, 50 parts of 10% aqueous solution of polyvinyl alcohol, and 25 parts of water are mixed and then wet pulverized until the mean particle size comes to 5 μm or smaller to give a flowable for each compound.

The following test examples will demonstrate that the present compounds are useful as the active ingredients of herbicides. The present compounds are designated by their compound numbers shown in Table 1.

The herbicidal activity and phytotoxicity are evaluated at 6 levels with indices of 0 to 5, i.e., shown by numeral "0", "1", "2", "3", "4", or "5", wherein "0" means that there was no or little difference in the degree of germination or growth between the treated plants (i.e., weeds and crops) and the untreated plants at the time of examination, and "5" means that the test plants died completely or their germination or growth was completely inhibited. The herbicidal activity is excellent when ranked at "4" or "5", but insufficient when ranked at "3" or lower. The phytotoxicity is not significant for practical use when ranked at "0" or "1", but not allowed when ranked at "2" or higher.

Test Example 1 Foliar Treatment on Upland Fields

Cylindrical plastic pots each having a diameter of 10 cm and a depth of 10 cm were filled with soil, and then seeded with barnyardgrass (*Echino-chloa crus-galli*), ivyleaf morningglory (*Ipomoea hederacea*), and velvetleaf (*Abutilon theophrasti*). These test plants were grown in a greenhouse for 19 days. Each of the test compounds listed below was formulated into an emulsifiable concentrate according to Formulation Example 2, and then diluted in its prescribed amount with water containing a spreading agent. The dilution was uniformly sprayed over the foliage of the test plants with a sprayer at a rate of 1000 liters per hectare After the application, the test plants were grown in the greenhouse for 19 days, and the herbicidal activity was examined. The results are shown in Table 2.

TABLE 2

| Test compound | Application amount of active ingredient (g/ha) | Herbicidal activity | | |
|---|---|---|---|---|
| | | barnyard-grass | ivyleaf morningglory | velvetleaf |
| 268 | 500 | 5 | 5 | 5 |
| 269 | 500 | 5 | 5 | 5 |
| 271 | 500 | 5 | 5 | 5 |
| 272 | 500 | 5 | 5 | 5 |
| 274 | 500 | 4 | 5 | 5 |
| 291 | 500 | 5 | 5 | 5 |
| 294 | 500 | 5 | 5 | 5 |
| 295 | 500 | 5 | 5 | 5 |
| 327 | 500 | 5 | 5 | 5 |

Test Example 2 Soil Surface Treatment on Upland Fields

Cylindrical plastic pots each having a diameter of 10 cm and a depth of 10 cm were filled with soil, and then seeded with barnyardgrass (*Echino-chloa crus-galli*), ivyleaf morningglory (*Ipomoea hederacea*), and velvetleaf (*Abutilon theophrasti*). Each of the test compounds listed below was formulated into an emulsifiable concentrate according to Formulation Example 2, and then diluted in its prescribed amount with water. The dilusion was uniformly sprayed over the soil surface in the pots with a sprayer at a rate of 1000 liters per hectare After the application, the test plants were grown in a greenhouse for 19 days, and the herbicidal activity was examined. The results are shown in Table 3.

TABLE 3

| Test compound | Application amount of active ingredient (g/ha) | Herbicidal activity | | |
|---|---|---|---|---|
| | | barnyard-grass | ivyleaf morningglory | velvetleaf |
| 268 | 2000 | 5 | 5 | 5 |
| 269 | 2000 | 5 | 5 | 5 |
| 271 | 2000 | 5 | 5 | 5 |
| 272 | 2000 | 5 | 5 | 5 |
| 274 | 2000 | 5 | 5 | 5 |
| 291 | 2000 | 5 | 5 | 5 |
| 294 | 2000 | 5 | 5 | 5 |
| 295 | 2000 | 5 | 5 | 5 |
| 327 | 2000 | 5 | 5 | 5 |

Test Example 3 Flooding Treatment on Paddy Fields

Cylindrical plastic pots each having a diameter of 9 cm and a depth of 11 cm were filled with soil, and then seeded with barnyardgrass (*Echino-chloa oryzicola*). These pots were flooded to form paddy fields, and the test plants were grown in a greenhouse for 7 days. Each of the test compounds listed below was formulated into an emulsifiable concentrate according to Formulation Example 2, and then diluted in its prescribed amount with water. The dilution was applied to the water surface in the pots at a rate of 50 liter per are. After the application, the test plants were grown in the greenhouse for 16 days, and the herbicidal activity was examined. The results are shown in Table 4.

TABLE 4

| Test compound | Application amount of active ingredient (g/ha) | Herbicidal activity barnyard-grass |
|---|---|---|
| 268 | 250 | 5 |
| 269 | 250 | 5 |
| 271 | 250 | 5 |
| 272 | 250 | 5 |
| 274 | 250 | 5 |
| 291 | 250 | 5 |
| 294 | 250 | 5 |
| 295 | 250 | 5 |
| 327 | 250 | 5 |

Test Example 4 Foliar Treatment on Upland Fields

Plastic pots each having an area of 25×18 cm$^2$ and a depth of 7 cm were filled then seeded with rice (*Oryza sativa*) and barnyardgrass (*Echinochloa crus-galli*). These test plants were grown for 15 days. The test compound described below was formulated into an emulsifiable concentrate according to Formulation Example 2, and then diluted in its prescribed amount with water. The dilution was uniformly sprayed over the foliage of the test plants with a sprayer at a rate of 1000 liters per hectare. At this time, the weeds and crops, although their growth was a different levels depending upon the grass species, were in the one- to three-leave stage and had different grass heights of 8 to 15 cm. After 24 days from the application, the herbicidal activity and phytotoxicity were examined. The results are shown in Table 5. The test was carried out in a greenhouse over the whole period.

TABLE 5

| Test compound | Application amount of active ingredient (g/ha) | Phytotoxicity on crops rice | Herbicidal activity barnyard grass |
|---|---|---|---|
| 271 | 63 | 0 | 5 |

We claim:
1. A pyridazin-3-one compound of formula (1):

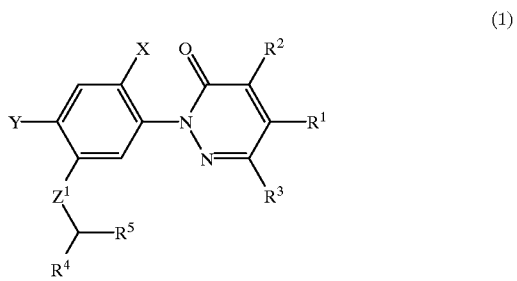

(1)

wherein R$^1$ is C$_1$–C$_3$ haloalkyl;
R$^2$ and R$^3$ are the same or different, and are independently hydrogen, C$_1$–C$_3$ alkyl, C$_1$–C$_3$ haloalkyl, or C$_1$–C$_3$ alkoxy C$_1$–C$_3$ alkyl;

X is hydrogen or halogen;

Y is halogen, nitro, cyano, or trihalomethyl;

$Z^1$ is oxygen, sulfur, or NH;

$R^4$ is hydrogen, halogen or $C_1-C_6$ alkyl;

and $R^5$ is formyl, formyl $C_1-C_6$ alkyl, formyl $C_2-C_6$ alkenyl, $C_1-C_6$ alkyl substituted with $OR^6$ and $OR^7$ on the same carbon atom, $C_2-C_6$ alkenyl substituted with $OR^6$ and $OR^7$ on the same carbon atom, $C_1-C_6$ alkyl substituted with $SR^6$ and $SR^7$ on the same carbon atom, $C_2-C_6$ alkenyl substituted with $SR^6$ and $SR^7$ on the same carbon atom, ($C_1-C_6$ alkyl) carbonyl $C_2-C_6$ alkenyl, ($C_1-C_6$ haloalkyl) carbonyl $C_2-C_6$ alkenyl, {($C_1-C_4$ alkoxy) $C_1-C_4$ alkyl} carbonyl $C_2-C_6$ alkenyl, or ($C_3-C_8$ cycloalkyl) carbonyl $C_2-C_6$ alkenyl, $R^6$ and $R^7$ are the same or different, and are independently $C_1-C_6$ alkyl or $C_1-C_6$ haloalkyl.

2. A pyridazin-3-one compound according to claim 1, wherein $Z^1$ is oxygen.

3. A pyridazin-3-one compound according to claim 1 or 2, wherein Y is halogen, $R^1$ is trifluoromethyl, $R^2$ is hydrogen or methyl, $R^3$ is hydrogen, and $R^4$ is hydrogen or methyl.

4. A pyridazin-3-one compound according to claim 3, wherein X is fluorine.

5. A pyridazin-3-one compound according to claim 1, 2, 3 or 4, wherein $R^4$ is hydrogen.

6. A pyridazin-3-one compound according to claim 1, 2, 3, 4 or 5, wherein $R^5$ is formyl or $C_1-C_6$ alkyl substituted with $OR^6$ and $OR^7$ on the same carbon atom, $R^6$ and $R^7$ are the same or different, and are independently $C_1-C_6$ alkyl.

7. A pyridazin-3-one compound according to claim 1, wherein $R^1$ is a group of $CF_2J$, and J is hydrogen, fluorine, chlorine, or trifluoromethyl.

8. A pyridazin-3-one compound according to claim 1, wherein $R^1$ is trifluoromethyl.

9. A herbicide comprising a pyridazin-3-one compound as set forth in any one of claims 1, 2, 3, 4, 5, 6, 7, and 8 as an active ingredient.

10. A method for controlling weeds, which comprises applying an effective amount of a pyridazin-3-one compound as set forth in any one of claims 1, 2, 3, 4, 5, 6, 7, and 8, to the weeds or to a place where the weeds are growing or will grow.

* * * * *